United States Patent
Noble et al.

(10) Patent No.: US 11,990,222 B2
(45) Date of Patent: May 21, 2024

(54) PATIENT CUSTOMIZED ELECTRO-NEURAL INTERFACE MODELS FOR MODEL-BASED COCHLEAR IMPLANT PROGRAMMING AND APPLICATIONS OF SAME

(71) Applicant: VANDERBILT UNIVERSITY, Nashville, TN (US)

(72) Inventors: Jack H. Noble, Nashville, TN (US); Ahmet Cakir, Nashville, TN (US); Benoit M. Dawant, Nashville, TN (US); Robert F. Labadie, Nashville, TN (US); Rene H. Gifford, Franklin, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 287 days.

(21) Appl. No.: 17/637,875

(22) PCT Filed: Aug. 26, 2020

(86) PCT No.: PCT/US2020/047884
§ 371 (c)(1),
(2) Date: Feb. 24, 2022

(87) PCT Pub. No.: WO2021/041466
PCT Pub. Date: Mar. 4, 2021

(65) Prior Publication Data
US 2022/0285005 A1    Sep. 8, 2022

Related U.S. Application Data

(60) Provisional application No. 62/891,480, filed on Aug. 26, 2019.

(51) Int. Cl.
G16H 20/40     (2018.01)
A61B 6/03      (2006.01)
(Continued)

(52) U.S. Cl.
CPC .............. *G16H 20/40* (2018.01); *A61B 6/032* (2013.01); *A61B 6/12* (2013.01); *A61B 6/501* (2013.01);
(Continued)

(58) Field of Classification Search
CPC .. G16H 20/40; G06T 7/55; G06T 7/73; G06T 7/33; G06T 2207/10081;
(Continued)

(56) References Cited

U.S. PATENT DOCUMENTS 6,068,652 A *  5/2000  Cohen ................ A61N 1/36038
                                              607/57
6,289,247 B1 *  9/2001  Faltys ................ A61N 1/36038
                                              607/57

(Continued)

FOREIGN PATENT DOCUMENTS

WO    2018200447 A1    11/2018
WO    WO-2018200447 A1 *  11/2018 ............. A61B 34/10

OTHER PUBLICATIONS

American Speech-Language Hearing Association (2008). Incidence and prevalence of hearing loss and hearing aid use in the United States—2008 edition.

(Continued)

*Primary Examiner* — Michael I Ezewoko
(74) *Attorney, Agent, or Firm* — Locke Lord LLP; Tim Tingkang Xia, Esq.

(57) ABSTRACT

Systems and methods are provided for performing model-based cochlear implant programming (MOCIP) on a living subject with a cochlear implant (CI) to determine stimulation settings of a patient-customized electro-neural interface (ENI) model. The method includes: localizing an electrode array of the CI and intracochlear structures of the living subject to determine patient-specific electrode positions of
(Continued)

the CI and a patient-specific anatomy shape; generating a CI electric field model based on the patient-specific electrodes positions of the CI and the patient-specific anatomy shape; and establishing an auditory nerve fiber (ANF) bundle model using the CI electric field model, and estimating neural health of the living subject using the ANF bundle model applications of the same.

29 Claims, 15 Drawing Sheets

(51) Int. Cl.
*A61B 6/12* (2006.01)
*A61B 6/50* (2024.01)
*A61N 1/05* (2006.01)
*G06F 30/23* (2020.01)
*G06T 7/33* (2017.01)
*G06T 7/55* (2017.01)
*G06T 7/73* (2017.01)
*A61B 34/10* (2016.01)

(52) U.S. Cl.
CPC ............ *A61B 6/506* (2013.01); *A61N 1/0541* (2013.01); *G06F 30/23* (2020.01); *G06T 7/33* (2017.01); *G06T 7/55* (2017.01); *G06T 7/73* (2017.01); *A61B 2034/102* (2016.02); *A61B 2034/105* (2016.02); *G06T 2207/10081* (2013.01); *G06T 2207/30052* (2013.01); *G06T 2207/30172* (2013.01)

(58) Field of Classification Search
CPC . G06T 2207/30052; G06T 2207/30172; G06F 30/23; A61B 6/032; A61B 6/12; A61B 6/501; A61B 6/506; A61B 2034/102; A61B 2034/105; A61N 1/0541
See application file for complete search history.

(56) References Cited

U.S. PATENT DOCUMENTS

| | | | | |
|---|---|---|---|---|
| 7,251,530 | B1 * | 7/2007 | Overstreet | A61N 1/36038 607/137 |
| 7,292,891 | B2 * | 11/2007 | Hartley | A61N 1/36038 607/57 |
| 7,292,892 | B2 * | 11/2007 | Litvak | A61N 1/36039 607/57 |
| 7,747,329 | B2 * | 6/2010 | Litvak | A61N 1/36039 607/57 |
| 7,805,198 | B2 * | 9/2010 | Overstreet | A61N 1/36038 607/57 |
| 7,920,925 | B2 * | 4/2011 | Overstreet | A61N 1/36038 607/57 |
| 8,024,046 | B2 * | 9/2011 | Litvak | A61N 1/36039 607/57 |
| 8,160,328 | B2 * | 4/2012 | Goetz | A61N 1/37247 382/128 |
| 8,180,129 | B2 * | 5/2012 | Goetz | A61N 1/36185 382/128 |
| 8,406,890 | B2 * | 3/2013 | Goetz | G06T 17/20 607/59 |
| 8,747,447 | B2 * | 6/2014 | Stafford | A61N 1/36039 607/88 |
| 8,862,240 | B2 * | 10/2014 | Goetz | A61N 1/37247 607/30 |
| 8,934,986 | B2 * | 1/2015 | Goetz | A61B 34/20 607/59 |
| 8,995,731 | B2 * | 3/2015 | Joglekar | A61B 6/12 382/128 |
| 9,044,588 | B2 * | 6/2015 | Conn | A61N 1/0558 |
| 9,055,974 | B2 * | 6/2015 | Goetz | A61N 1/37247 |
| 9,259,589 | B2 * | 2/2016 | Goetz | A61N 1/37247 |
| 9,572,981 | B2 * | 2/2017 | Noble | G06T 7/337 |
| 9,814,885 | B2 * | 11/2017 | Molnar | A61N 1/36185 |
| 10,516,953 | B2 * | 12/2019 | Conn | A61F 2/18 |
| 10,546,388 | B2 * | 1/2020 | Noble | A61B 34/10 |
| 10,549,094 | B2 * | 2/2020 | Johnston | A61B 5/053 |
| 10,821,284 | B2 * | 11/2020 | Noble | A61N 1/36039 |
| 11,027,129 | B2 * | 6/2021 | Noble | G16H 20/40 |
| 11,071,869 | B2 * | 7/2021 | Leigh | A61N 1/37223 |
| 11,406,826 | B2 * | 8/2022 | Noble | A61N 1/0541 |
| 11,484,218 | B2 * | 11/2022 | Johnston | A61B 5/7282 |
| 11,510,014 | B2 * | 11/2022 | Smith | A61N 1/36036 |
| 11,577,078 | B2 * | 2/2023 | Conn | H04R 25/407 |
| 11,813,460 | B2 * | 11/2023 | Smith | A61N 1/36038 |
| 2007/0293785 | A1 * | 12/2007 | Litvak | A61N 1/36039 600/559 |
| 2009/0012580 | A1 * | 1/2009 | Arnoldner | A61N 1/36038 607/57 |
| 2010/0070000 | A1 * | 3/2010 | Litvak | A61N 1/36038 607/57 |
| 2011/0238176 | A1 * | 9/2011 | Bradley | A61N 1/0541 623/10 |
| 2011/0319965 | A1 * | 12/2011 | Fridman | A61N 1/36039 607/57 |
| 2015/0088225 | A1 * | 3/2015 | Noble | A61N 1/36185 607/57 |
| 2017/0157400 | A1 * | 6/2017 | Noble | A61B 34/10 |
| 2018/0311501 | A1 * | 11/2018 | Noble | A61N 1/36039 |
| 2020/0138520 | A1 * | 5/2020 | Noble | G06T 11/005 |
| 2020/0139125 | A1 * | 5/2020 | Noble | G16H 50/50 |

OTHER PUBLICATIONS

Buss E, Pillsbury HC, Buchman CA, Pillsbury CH, Clark MS, Haynes DS, Labadie RF, Amberg S, Roland PS, Kruger P, Novak MA, Wirth JA, Black JM, Peters R, Lake J, Wackym PA, Firszt JB, Wilson BS, Lawson DT, Schatzer R, S. DHP, Barco AL: Multicenter U.S. Bilateral med-el cochlear implantation study: Speech perception over the first year of use. Ear Hear 2008;29:20-32.
Dorman MF, Yost W, Wilson BS, Gifford RH: Speech perception and sound localization by adults with bilateral cochlear implants. Seminars in Hearing 2009;32:73-89.
Gifford RH, Shallop JK, Peterson AM. (2008). Speech Recognition Materials and Ceiling Effects: Considerations for Cochlear Implant Programs. Audiol Neurotol, 13:193-205.
Dorman MF, Sheffield SW, Teece K, Olund AP, Gifford RH. (in press). Availability of binaural cues for bilateral cochlear implant recipients and bimodal listeners with and without hearing preservation. Audiol Neurotol.
Litovsky RY, Parkinson A, Arcaroli J, Sammeth C: Simultaneous bilateral cochlear implantation in adults: A multicenter clinical study. Ear Hear 2006;27:714-730.
Michelle Hughes. Objective measures in cochlear implants, 1st edition. Plural publishing, 2012.
Rubenstein J.T., "How cochlear implants encode speech," Curr Opin Otolaryngol Head Neck Surg. 12(5): 444-8, 2004.
Srijata Chakravorti and Jack H. Noble (co-first authors), René H. Gifford, Benoit M. Dawant, Brendan O'Connell, Jianing Wang, Robert F. Labadie, "Further evidence of the relationship between cochlear implant electrode positioning and hearing outcomes," Otology & Neurotology, Jun. 2019—vol. 40—Issue 5—p. 617-624.
Holden LK, Finley CC, Firszt JB, Holden TA, Brenner C, Potts LG, Gotter BD, Vanderhoof SS, Mispagel K, Heydebrand G, Skinner MW., "Factors affecting open-set word recognition in adults with cochlear implants," Ear Hear. 34(3):342-60, 2013.
Jack Noble and Robert Labadie, "Preliminary results with image-guided cochlear implant insertion techniques," Otology & Neurotology, vol. 39(7), pp. 922-928, 2018.
Wilson B.S., Finley C.C., Lawson, D.T., Wolford, R.D., Eddington, D.K., Rabinowitz, W.M., "Better speech recognition with cochlear implants," Nature 352, 236-238, 1991.
Bierer JA (2007). Threshold and channel interaction in cochlear implant users: evaluation of the tripolar electrode configuration. J Acoust Soc Am, 121(3): 1642-53.

(56) References Cited

OTHER PUBLICATIONS

Bierer JA (2010). Probing the electrode-neuron interface with focused cochlear implant stimulation. Trends Amplif, 14(2): 84-95.
Noble JH, Labadie RF, Majdani O, Dawant BM,. Automatic segmentation of intra-cochlear anatomy in conventional CT. IEEE Trans. on Biomedical. Eng. 58(9), 2011. : 2625-32. PMID 21708495.
Noble, J.H., Gifford, R.H., Labadie, R.F., Dawant, B.M., "Statistical Shape Model Segmentation and Frequency Mapping of Cochlear Implant Stimulation Targets in CT," N. Ayache et al. (Eds.): MICCAI 2012, Part II, LNCS 7511, pp. 421-428. 2012. PMID 23286076.
Noble JH, Labadie RF, Gifford RH, Dawant BM, "Image-guidance enables new methods for customizing cochlear Implant stimulation strategies," IEEE Trans. on Neural Systems and Rehabilitation Engineering, vol. 21(5):820-9, 2013. PMID 23529109.
Noble JH, Gifford RH, Hedley-Williams AJ, Dawant BM, and , Labadie RF, "Clinical evaluation of an image-guided cochlear implant programming strategy," Audiology & Neurotology, vol. 19, pp. 400-411, 2014. PMC4305276.
Noble J.H., Hedley-Williams A.J., Sunderhaus L.W., Dawant B.M., Labadie R.F., Camarata S.M., Gifford R.H., "Initial results with image-guided cochlear implant programming in children," Otology & Neurotology 37(2), pp. 69-79, 2016. PMC4849538.
Fu, Q. J., Shannon, R. V., & Galvin, J. J. 3rd. (2002). Perceptual learning following changes in the frequency-to-electrode assignment with the Nucleus-22 cochlear implant. Journal of the Acoustical Society of America, 112 (4), 1664-1674.
Nadol, J. B., Young, Y. S., & Glynn, R. J. (1989). Survival of Spiral Ganglion Cells in Profound Sensorineural Hearing oss: Implications for Cochlear Implantation. Annals of Otology, Rhinology & Laryngology, 98(6), 411-416.
Mishaela DiNino, Gabrielle O'Brien, Steven M. Bierer, Kelly N. Jahn, Julie G. Arenberg, "The Estimated Electrode-Neuron Interface in Cochlear Implant Listeners Is Different for Early-Implanted Children and Late-Implanted Adults," Journal of the Association for Research in Otolaryngology, Jun. 2019, vol. 20, Issue 3, pp. 291-303.
Mendel LL, Mustain WD, Magro J, "Normative Data for the Maryland CNC Test," Journ. of Am. Acad. Audiol., vol. 25, pp. 775-781, 2014.
Kochkin S, "The efficacy of hearing aids in achieving compensation equity in the workplace," The Hearing Journal, vol. 63 (10), pp. 19-28, 2010.
Labadie RF, Noble JH, Hedley-Williams AJ, Sunderhaus LW, Dawant BM, Gifford RH. Results of Postoperative, CT-based, Electrode Deactivation on Hearing in Prelingually Deafened Adult Cochlear Implant Recipients. Otology & Neurotology Feb. 2016;37(2):137-45. PMC4712086.
Theodore R. McRackan, Jack H. Noble, Eric P. Wilkinson, Dawna Mills, Mary S. Dietrich, Benoit M. Dawant, Rene H. Gifford, Robert F. Labadie, "Implementation of Image-Guided Cochlear Implant Programming at a Distant Site," Otolaryngology—Head & Neck Surgery, vol. 156(5), pp. 933-937, 2017.PMID: 28374640.
Zhao Y, Dawant BM, Labadie RF, Noble JH. Automatic localization of cochlear implant electrodes in CT. Med Image Comput Comput Assist Interv. 2014;17(Pt 1):331-8. PMC4426961.
Noble, J.H. and Dawant, B.M., "Automatic graph-based localization of cochlear implant electrodes in CT," Lecture Notes in Computer Science—Proceedings of MICCAI, vol. 9350, pp. 152-159, 2015. PMC4854292.
Zhao Y, Dawant BM, Noble JH. Automatic selection of the active electrode set for image-guided cochlear implant programming. Journal of medical imaging Jul. 2016;3(3):035001 PMC5031788.
Zhang D, Liu Y, Noble JH, Dawant BM. Localizing landmark sets in head CTs using random forests and a heuristic search algorithm for registration initialization. Journal of medical imaging. Oct. 2017;4(4):044007. PMC5722233.
Zhang D, Zhao Y, Noble JH, Dawant BM. Selecting electrode configurations for image-guided cochlear implant programming using template matching. Journal of medical imaging. Apr. 2018;5(2):021202. PMC5724566.
Y Zhao, S Chakravorti, RF Labadie, BM Dawant, JH Noble, "Automatic graph-based method for localization of cochlear implant electrode arrays in clinical CT with sub-voxel accuracy," Medical image analysis, vol. 52, pp. 1-12, 2019.
Yiyuan Zhao, Robert Labadie, Benoit Dawant, Jack Noble, "Validation of cochlear implant electrode localization techniques using uCTs," J. of Medical Imaging, 5(3), 035001 (2018).
Yiyuan Zhao, Benoit Dawant, and Jack Noble., "Automatic localization of closely-spaced cochlear implant electrode arrays in clinical CTs," Med. Phys., vol. 45 (11), pp. 5030-5040, 2018.
Chakravorti S, Bussey BJ, Zhao Y, Dawant BM, Labadie RF, Noble JH. Cochlear implant phantom for evaluating computed tomography acquisition parameters. Journal of medical imaging. Oct. 2017;4(4):045002. PMC5689133.
Cakir A, Labadie RF, Zuniga MG, Dawant BM, Noble JH. Evaluation of Rigid Cochlear Models for Measuring Cochlear Implant Electrode Position. Otology and Neurotology. Dec. 2016;37(10):1560-1564. PMC5240585.
Connell BP, Cakir A, Hunter JB, Francis DO, Noble JH, Labadie RF, Zuniga G, Dawant BM, Rivas A, Wanna GB. Electrode Location and Angular Insertion Depth are Predictors of Audiologic Outcomes in Cochlear Implantation. Otology & neurotology, Sep. 2016,37(8):1016-23. PMC4983244.
Connell BP, Hunter JB, Gifford RH, Rivas A, Haynes DS, Noble JH, Wanna GB. Electrode Location and Audiologic Performance After Cochlear Implantation: A Comparative Study Between Nucleus CI422 and CI512 Electrode Arrays. Otology and Neurotology. Sep. 2016,37(8):1032-5. PMC4988342.
Zuniga MG, Rivas A, Hedley-Williams A, Gifford RH, Dwyer R, Dawant BM, Sunderhaus LW, Hovis KL, Wanna GB, Noble JH, Labadie RF. Tip Fold-over in Cochlear Implantation: Case Series. Otology and Neurotology. Feb. 2017;38(2):199-206. PubMed PMID: 27918363.
Rivas A, Cakir A, Hunter JB, Labadie RF, Zuniga MG, Wanna GB, Dawant BM, Noble JH. Automatic Cochlear Duct Length Estimation for Selection of Cochlear Implant Electrode Arrays. Otology and Neurotology. Mar. 2017;38(3):339-346. PMC5335919.
Wang J, Dawant BM, Labadie RF, Noble JH. Retrospective Evaluation of a Technique for Patient-Customized Placement of Precurved Cochlear Implant Electrode Arrays. Otolaryngology—head and neck surgery. Mar. 1, 2017;:194599817697298. PMID: 28374623.
Connell BP, Hunter JB, Haynes DS, Holder JT, Dedmon MM, Noble JH, Dawant BM, Wanna GB. Insertion depth Impacts speech perception and hearing preservation for lateral wall electrodes. The Laryngoscope. Mar. 17, 2017.
BP O'Connell, MT Dillon, JH Noble, GB Wanna, ER King, HC Pillsbury, KB Brown, "Insertion depth impacts speech perception and hearing preservation outcomes for lateral wall electrodes," Journal of Hearing Science, vol. 8(2), 2018.
Kanthaiah Koka, William Jason Riggs, Robert Dwyer, Jourdan Taylor Holder, Jack H Noble, Benoit M Dawant, Amanda Ortmann, Carla V Valenzuela, Jameson K Mattingly, Michael M Harris, Brendan P O'Connell, Leonid M Litvak, Oliver F Adunka, Craig Alan Buchman, Robert F Labadie, "Intra-Cochlear Electrocochleography During Cochear Implant Electrode Insertion Is Predictive of Final Scalar Location," Otology & Neurotology vol. 39(8) pp. e654-e659, 2018.
Rene H Gifford, Jack H Noble, Stephen M Camarata, Linsey W Sunderhaus, Robert T Dwyer, Benoit M Dawant, Mary S Dietrich, Robert F Labadie, "The relationship between spectral modulation detection and speech recognition: Adult versus pediatric cochlear implant recipients," Trends in Hearing, vol. 22, 2018.
Holder JT, Kessler DM, Noble JH, Gifford RH, Labadie RF, "Prevalence of Extracochlear Electrodes: Computerized Tomography Scans, Cochlear Implant Maps, and Operative Reports," Otology & Neurotology, vol. 39(5), e325-e331, 2018.
Davis TJ, Zhang D, Gifford RH, Dawant BM, Labadie RF, Noble JH. Relationship Between Electrode-to-Modiolus Distance and Current Levels for Adults With Cochlear Implants. Otol Neurotol. Jan. 2016;37(1):31-37. PMCID: PMC4675044.

(56) References Cited

OTHER PUBLICATIONS

Ahmet Cakir, Robert T Dwyer, Jack H Noble, "Evaluation of a high-resolution patient-specific model of the electrically stimulated cochlea," Journal of Medical Imaging, vol. 4(2), 025003, 2017.
T. F. Cootes, C. J. Taylor, C. H. Cooper, and J. Graham, Active shape models-their training and application. Computer Vision and Image Understanding, vol. 61, 1995. pp. 38-59.
The Length of the Organ of Corti in Man, Hardy M, American Journal of Anatomy, 62(2), 1938, p. 179-311.
Korean Intellectual Property Office (ISR/KR), "International Search Report for PCT/US2020/047884", Korea, dated Dec. 2, 2020.
Cakir, Ahmet, 'Use of patient-specific models for computer-assisted cochlear implant programming', Dissertation for the degree of doctor in Vanderbilt University, Jul. 17, 2019, pp. 1-168.
Cakir, Ahmet et al., 'P3: auditory neural health imaging (anhi) using patient-customized models', 2019 Conference on Implantable Auditory Prostheses, Jul. 15, 2019, p. 30.
Devries, Lindsay et al., 'Assessing the electrode-neuron interface with the electrically evoked compound action potential, electrode position, and behavioral thresholds', Journal of the Association for Research in Otolaryngology, 2016, vol. 17, pp. 237-252.
Jahn, Kelly N. et al., 'Evaluating psychophysical polarity sensitivity as an indirect estimate of neural status in cochlear implant listeners', Journal of the Association for Research in Otolaryngology, Apr. 4, 2019, vol. 20, pp. 415-430.
Pelosi S and Noble J (co-first authors), Dawant B, and Labadie RF. "Analysis of inter-subject variations in promontory and intracochlear anatomy for cochlear implantation," Otology and Neurotology vol. 34(9), pp. 1675-1680, 2013.
Wanna, G.B., Noble J.H., Carlson, M.L., Gifford, R.H., Dietrich, M.S., Haynes, D.S. Dawant, B.M., and Labadie, R.F., "Impact of Electrode Design and Surgical Approach on Scalar Location and Cochlear Implant Outcomes," Laryngoscope, vol. 124(S6), pp. S1-S7, 2014.
Wanna GB, Noble JH, Gifford RH, Dietrich MS, Sweeney AD, Zhang D, Dawant BM, Rivas A, Labadie RF. "Impact of Intrascalar Electrode Location, Electrode Type, and Angular Insertion Depth on Residual Hearing in Cochlear Implant Patients: Preliminary Results." Otol Neurotol. 36(8):1343-8, 2015.
F.L. Bookstein, "Principal warps: Thin-plate splines and the decomposition of deformations," IEEE Transactions on Pattern Analysis and Matching Intelligence, vol. 11(6), 1989, pp. 567-585.
Whiten D, "Electro-anatomical models of the cochlear implant," Ph.D. Thesis, Massachusetts Institute of Technology Library, 2007.
Rattay F, Lutter P, Felix H., "A model of the electrically excited human cochlear neuron. I. Contribution of neural substructures to the generation and propagation of spikes," Hearing Research; 153; 43-63, 2001.
Rattay, F., "Basics of hearing theory and noise in cochlear implants," Chaos Solitons Fractals 11: 1875-84, 2000.
Li PM, Somdas MA, Eddington DK, Nadol JB Jr. Analysis of intracochlear new bone and fibrous tissue formation in human subjects with cochlear implants. Ann Otol Rhinol Laryngol. Oct. 2007;116(10):731-8. PMID: 17987778.
Zwolan T.A., Collins L.M., Wakefiled G.H., "Electrode discrimination and speech recognition in postlingually deafened adult cochlear implant subjects," J. Acoust. Soc. Am. 102(6): 3673-85, 1997.
Long, C. J., Holden, T. A., McClelland, G. H., Parkinson, W. S., Shelton, C., Kelsall, D. C., . . . Smith, Z. M. (2014). Examining the electro-neural interface of cochlear implant users using psychophysics, CT scans, and speech understanding. Journal of the Association for Research in Otolaryngology: JARO, 15(2), 293-304. (PMID:24477546).
Peterson GE, Lehiste I. (1962). Revised CNC lists for auditory tests. J Speech Hear Disord. 27:62-70.
Spahr A.J., Dorman M.F., Litvak L.M., Van Wie S., Gifford R.H., Loizou P.C., Loiselle L.M., Oakes T., Cook S., "Development and validation of the AzBio sentence lists," Ear Hear. 33(1): 112-7, 2012.
Saoji AA, Litvak L, Spahr AJ, Eddins DA. (2009). Spectral modulation detection and vowel and consonant dentifications in cochlear implant listeners. J Acoust Soc Am. 126(3):955-8.
Henry B.A., Turner C.W., "The resolution of complex spectral patterns by cochlear implant and normal-hearing listeners," J Acoust Soc Am 113(5):2861-73, 2003.
Drennan WR, Won JH, Nie K, Jameyson E, Rubinstein JT. (2010). Sensitivity of psychophysical measures to signal processor modifications in cochlear implant users. Hear Res. 262(1-2):1-8.
Gifford RH, Hedley-Williams, A, Spahr, AJ. Clinical assessment of spectral modulation detection for cochlear implant recipients: a non-language based measure of performance outcomes. Int J Audiol. Mar. 2014;53(3):159-64.
Cox RM, Alexander GC. (1995). The abbreviated profile of hearing aid benefit. Ear Hear. 16(2):176-86.
Berenstein CK, Mens LH, Mulder JJ, Vanpoucke FJ. (2008). Current steering and current focusing in cochlear Implants: comparison of monopolar, tripolar and virtual channel electrode configurations. Ear Hear. 29(2):250-60.
Landsberger DM, Padilla M, Srinivasan AG. (2012). Reducing current spread using current focusing in cochlear mplant users. Hear Res. 284(1-2):16-24.
Srinivasan AG, Padilla M, Shannon RV, Landsberger DM. (2013). Improving speech perception in noise with current focusing in cochlear implant users. Hear Res.299:29-36.
Baer and Moore, 1994 T. Baer and B.C.J. Moore, Effects of spectral smearing on the intelligibility of sentences in the presence of interfering speech. J. Acoust. Soc. Am., 95 (1994), pp. 2277-2280.
Stakhovskaya O, Spridhar D, Bonham BH, Leake PA. Frequency Map for the Human Cochlear Spiral Ganglion: Implications for Cochlear Implants. Journ. Assoc. Res. Otol. 8, 2007. : 220-233.
MSTB: The new minimum speech test battery. http://auditorypotential.com/MSTB.html, 2011.
Tyler R.S., Preece J.P., Lansing C.R., Otto S.R., Gantz B.J., "Previous experience as a confounding factor in comparing cochlear-implant processing schemes," J. Speech Hear. Res. 29: 282-7, 1986.
Carnevale, N.T. and Hines, M.L. The Neuron Book. Cambridge, UK: Cambridge University Press, 2006.

* cited by examiner

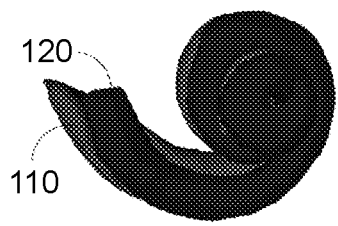
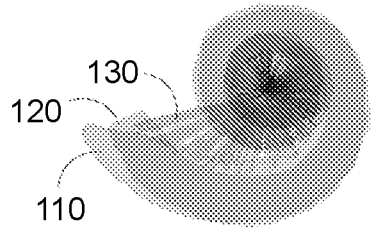
FIG. 1A  FIG. 1B
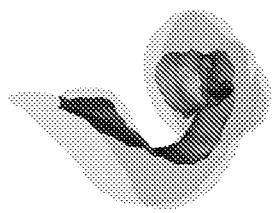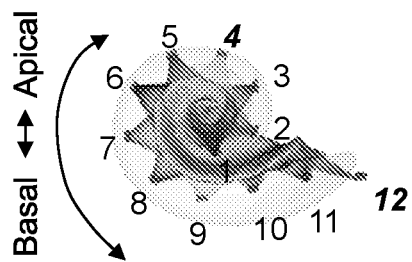
FIG. 1C  FIG. 1D
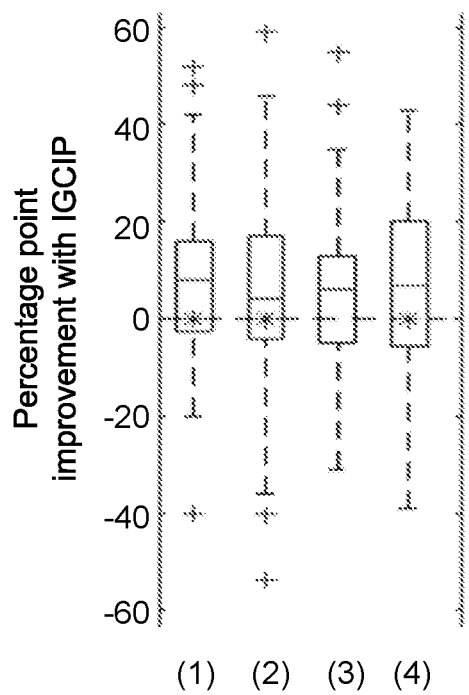
FIG. 2

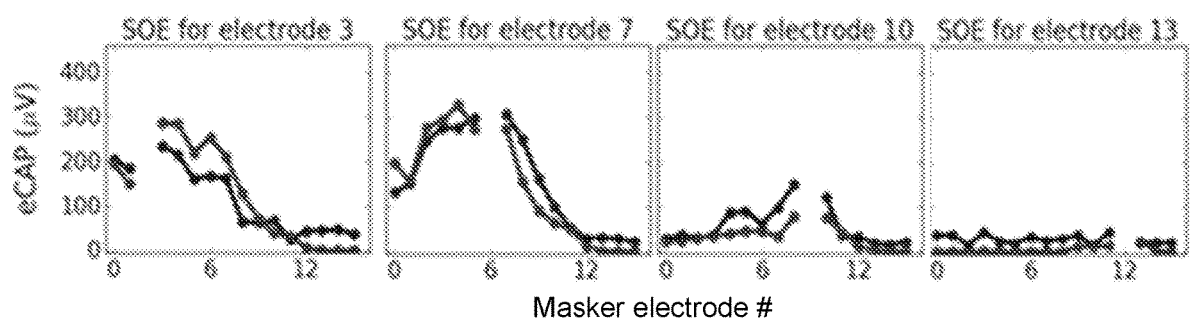
FIG. 17
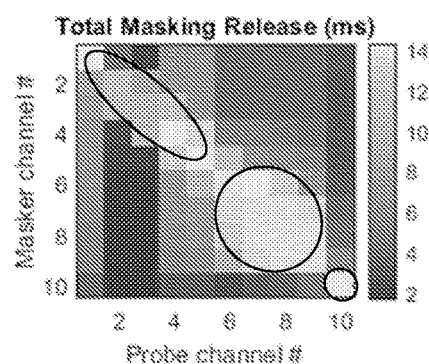 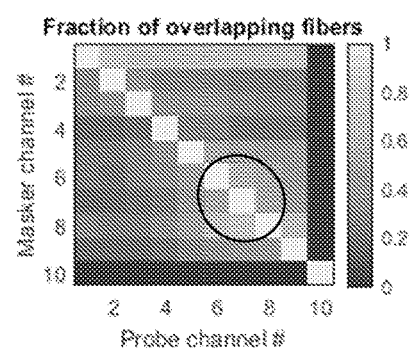
FIG. 19  FIG. 20

PATIENT CUSTOMIZED ELECTRO-NEURAL INTERFACE MODELS FOR MODEL-BASED COCHLEAR IMPLANT PROGRAMMING AND APPLICATIONS OF SAME

CROSS-REFERENCE TO RELATED PATENT APPLICATIONS

This PCT application claims priority to and the benefit of U.S. Provisional Patent Application Ser. No. 62/891,480, filed Aug. 26, 2019. The above-identified application is incorporated herein by reference in its entirety.

Some references, which may include patents, patent applications, and various publications, are cited and discussed in the description of the invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference.

STATEMENT AS TO RIGHTS UNDER FEDERALLY-SPONSORED RESEARCH

This invention was made with government support under Grant Numbers DC014037, DC012620, DC008408 and DC014462, awarded by the National Institutes of Health. The Government has certain rights in the invention.

FIELD OF THE INVENTION

The invention relates generally to cochlear implant (CI) image processing technology, and more particularly to systems and methods for performing model-based CI programming (MOCIP) on patient-customized electro-neural interface (ENI) models and applications of the same.

BACKGROUND INFORMATION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

With over 500,000 recipients worldwide, cochlear implants (CIs) are considered standard of care treatment for severe-to-profound sensory-based hearing loss. In normal hearing, sound waves induce pressure oscillations in the cochlear fluids, which in turn initiate a traveling wave of displacement along the basilar membrane (BM). This membrane divides the cochlea along its length and produces maximal response to sounds at different frequencies. Because motion of BM is then sensed by hair cells which are attached to the BM, these sensory cells are fine-tuned to respond to different frequencies of the received sounds. The hair cells further pass signals to auditory nerve fibers (ANFs) by releasing chemical transmitters. Finally, the electrical stimulation is propagated along the ANFs to the auditory cortex allowing the brain to sense and process the sounds. For patients suffering sensorineural hearing loss, which is principally caused by damage or destruction of the hair cells, direct stimulation of the auditory nerve using a CI is possible if ANFs are intact. A CI replaces the hair cells with an externally worn signal processor that decomposes the incoming sound into signals sent to an electrode array that is surgically implanted into the cochlea, and the CI restore hearing by applying electric potential to neural stimulation sites in the cochlea with the implanted electrode array. After implantation, a sequence of CI programming (mapping) sessions with an audiologist is performed to attempt to optimize hearing performance. While results with these devices have been remarkably successful, a significant number of CI recipients experience poor speech understanding, and, even among the best performers, restoration to normal auditory fidelity is rare. It is estimated that less than 10% of those who could benefit from this technology pursue implantation, in large part due to the high-degree of uncertainty in outcomes.

Therefore, a heretofore unaddressed need exists in the art to address the aforementioned deficiencies and inadequacies.

SUMMARY OF THE INVENTION

One aspect of the present invention relates to a method for performing model-based cochlear implant programming (MOCIP) on a living subject with a cochlear implant (CI) to determine stimulation settings of a patient-customized electro-neural interface (ENI) model, which includes: localizing an electrode array of the CI and intracochlear structures of the living subject to determine patient-specific electrode positions of the CI and a patient-specific anatomy shape; generating a CI electric field model based on the patient-specific electrodes positions of the CI and the patient-specific anatomy shape; and establishing an auditory nerve fiber (ANF) bundle model using the CI electric field model, and estimating neural health of the living subject using the ANF bundle model.

In another aspect, the present invention relates to a system for performing MOCIP on a patient-customized ENI model, including: a computing device having a processor and a storage device storing computer executable instructions, wherein the computer executable instructions, when being executed by the processor, causes the processor to perform operations comprising: localizing an electrode array of a cochlear implant (CI) implanted on a living subject and intracochlear structures of the living subject to determine patient-specific electrode positions of the CI and a patient-specific anatomy shape; generating a CI electric field model based on the patient-specific electrodes positions of the CI and the patient-specific anatomy shape; and establishing an ANF bundle model using the CI electric field model, and estimating neural health of the living subject using the ANF bundle model.

In yet another aspect of the present invention, a non-transitory tangible computer-readable medium is provided for storing computer executable instructions which, when executed by one or more processors, cause a method for performing MOCIP on a living subject with a CI to determine stimulation settings of a patient-customized ENI model to be performed. The method includes: localizing an electrode array of the CI and intracochlear structures of the living subject to determine patient-specific electrode positions of the CI and a patient-specific anatomy shape; generating a CI electric field model based on the patient-specific electrodes positions of the CI and the patient-specific anatomy shape; and establishing an ANF bundle model using the CI electric field model, and estimating neural health of the living subject using the ANF bundle model.

In certain embodiments, the patient-specific anatomy shape is determined by: obtaining a plurality of micro computed tomography (µCT) images of a plurality of *cochleae* specimens; creating a non-rigid statistical shape model using the µCT images; fitting the non-rigid statistical shape model to an external boundary of the cochlea of the living subject in a computed tomography (CT) image of a cochlea of the living subject to localize positions of scala tympani (ST), scala vestibuli (SV) and modiolus of the living subject; and determining estimated positions of ANF bundles of the living subject.

In one embodiment, the µCT images include µCT images of at least 8 cochleae specimens.

In one embodiment, the estimated positions of the ANF bundles are determined by: delineating Rosenthal's Canal (RC) and internal auditory canal (IAC) in the µCT images; registering, with localized surfaces of the ST, the SV and the modiolus, estimations of fiber endpoints of the RC and the IAC delineated in the µCT images to the CT image using thin-plate splines; and tracing estimated fiber bundle paths of the ANF bundles from the fiber endpoints between the ST and the SV through the RC and out to the IAC.

In one embodiment, the patient-specific electrode positions of the CI are determined by identifying, from the µCT images, center lines of bright tubes or blobs representing the electrode array.

In certain embodiments, the generating the CI electric field model comprises: generating a tissue resistivity map for the living subject based on the patient-specific electrodes positions of the CI and the patient-specific anatomy shape; inputting the tissue resistivity map to a finite difference model to simulate electric fields created in tissues of the living subject when electrodes of the CI are activated; performing electric field imaging (EFI) to measure the actual electric fields sensed by other electrodes of the electrodes of the CI when one of the electrodes of the CI is activated as a current source; and optimizing resistivity values of the tissues in the tissue resistivity map based on the electric field simulated by the finite difference model and the actual electric fields measured by EFI.

In one embodiment, the optimizing the resistivity values of the tissues comprises: comparing, for each of the electrodes of the CI, the electric fields simulated by the finite difference model and the actual electric fields measured by EFI; and in response to determining, for a specific electrode of the electrodes, the electric field simulated by the finite difference model corresponding to the specific electrode is significantly lower than the actual electric fields measured by EFI corresponding to the specific electrode, determining tissue growth occurs at the specific electrode, and adding a soft tissue layer around the specific electrode in the finite difference model.

In certain embodiments, the estimating the neural health of the living subject comprises: establishing the ANF bundle model with a plurality of ANF bundles, wherein each of the ANF bundles includes a plurality of fibers; simulating electrically evoked compound action potentials (eCAPs) in each of the fibers of the ANF bundles; and estimating, for the electrodes of the CI, the ANF bundles activated by each of the electrodes in response to a given stimulus.

In one embodiment, each of the fibers in the ANF bundle model is a warmed Hodgkin-Huxley (wHH) fiber.

In one embodiment, the estimating the neural health of the living subject further comprises: measuring actual eCAPs for the electrodes of the CI; and tuning neural health parameters of the ANF bundle model based on differences of the eCAPs simulated and the actual eCAPs measured.

In one embodiment, the eCAPs are measured by amplitude growth functions (AGFs), spread of excitation (SOE) functions, and refractory recovery functions (RRFs).

In certain embodiments, the method further includes performing validation of the ANF bundle model by: training the ANF bundle model using the eCAPs measured by one of the AGFs, SOE functions and RRFs; and estimating the neural health of the living subject using the trained ANF bundle model by simulating the eCAPs measured by a different one of the AGFs, SOE functions and RRFs.

In certain embodiments, the method further includes performing validation of the ANF bundle model by: predicting perceptual psychophysical metrics of the living subject using the ANF bundle model; measuring model-estimated psychophysical metrics of the living subject; and calculating a correlation coefficient between the model-estimated psychophysical metrics and the perceptual psychophysical metrics.

In one embodiment, the psychophysical metrics includes channel overlap (CO) and tripolar thresholds.

These and other aspects of the invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 1A shows a cochlea having scala tympani and scala vestibule according to one embodiment of the invention.

FIG. 1B shows a rendering of the auditory nerve fibers (ANFs) of the cochlea as shown in FIG. 1A.

FIG. 1C shows the interface between the spiral ganglion (SG) nerve cells and the intra-cochlear cavities of the cochlea as shown in FIG. 1A.

FIG. 1D shows the implanted electrodes of a cochlear implant (CI) according to one embodiment of the invention.

FIG. 2 shows the benefit of Image-Guided Cochlear Implant Programming (IGCIP) according to one embodiment of the invention.

FIG. 17 shows eCAP SOE measured and simulated by the model according to one embodiment of the invention.

FIG. 19 shows a matrix of mask release times according to one embodiment of the invention.

FIG. 20 shows a matrix of channel overlap fraction according to one embodiment of the invention.

DETAILED DESCRIPTION OF THE INVENTION

Figure 3:
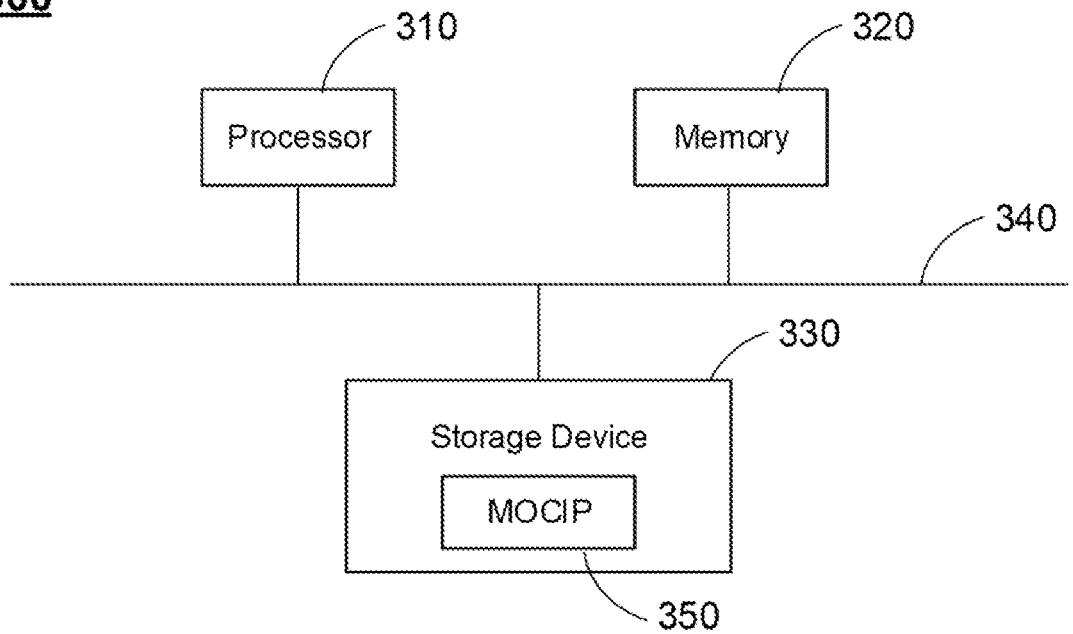
FIG. 3 schematically shows a system for performing model-based cochlear implant programming (MOCIP) on a patient-customized electro-neural interface (ENI) model according to one embodiment of the invention.

The invention will now be described more fully hereinafter with reference to the accompanying drawings, in which exemplary embodiments of the invention are shown. The invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. As used herein, the term "and/or" includes any and all combinations of one or more of the associated listed items.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

Overview of the Invention

As discussed above, the CI is the preferred treatment for over 1M individuals in the U.S. who experience severe-to-profound (SP) sensorineural hearing loss (HL) for which hearing aids are ineffective. For example, FIGS. 1A-1C show the cochlea, and FIG. 1D shows the CI according to one embodiment of the invention. Specifically, FIG. 1A shows the scala tympani 110 and scala vestibuli 120, the two principal cavities of the cochlea, and FIG. 1B shows a rendering of the auditory nerve fibers (ANFs) 130. FIG. 1C shows a surface representing the interface between the spiral ganglion (SG) nerve cells and the intra-cochlear cavities, with the tonotopic place frequencies of the SG in Hz. FIG. 1D shows the implanted electrodes of an electrode array in a CI, where the 12 implanted electrodes of the electrode array are respectively numbered 1-12, thus showing how current spreads from each implanted electrode before reaching the modiolus across the implanted electrodes. As shown in FIG. 1D, the main components of a CI are the electrode array that is surgically implanted into the cochlea, and an externally-worn processor (not shown), which converts sounds detected using a microphone into electrical signals that are sent to the appropriate contact in the electrode array to stimulate the SG nerve cells of the auditory nerve fibers (see FIG. 1C). Although FIG. 1D shows the electrode array with 12 electrodes, in certain embodiments, the electrode array may have up to 22 contacts depending on the manufacturer, dividing the available ANFs to, at most, 22 frequency bands or stimulation areas when using monopolar stimulation. The CI has arguably been the most successful neural prosthesis.

Implants available today yield remarkable speech recognition results for the majority of recipients with average word and sentence recognition approximating 60% and 70% correct, respectively, for unilaterally implanted recipients and 70% and 80% correct for bilateral recipients. Despite this success, outcomes are widely variable with a significant number of users receiving marginal benefit. Further, restoration to normal fidelity is rare even among the best performers.

A substantial portion of the variability in outcomes with CIs can be attributed to a sub-optimal electro-neural interface (ENI). In natural hearing, each neural channel (out of ~30,000 fibers) is tonotopically mapped, i.e., it is activated when its finely tuned characteristic frequency is present in a sound. Refractoriness limits maximum stimulation rate of each fiber to ~1 ms. With a CI, due to the small number of electrodes (12 to 22) and their wide current spread, spectral resolution is limited. Thus, each electrode stimulates nerves corresponding to a wide range of frequencies, and the neural populations recruited by neighboring electrodes are highly overlapping. Two factors ultimately determine the quality of the ENI: the health of the individual nerve fibers and the distance from the electrodes to neural stimulation sites. Electrodes that are close to healthy stimulation sites create finer excitation patterns and have a higher quality ENI, whereas electrodes that are distant to healthy sites create broad, overlapping excitation (see FIG. 1D). Overlap creates spectral smearing artifacts and, due to the refractoriness of the nerves, channel interaction distortions, where the set of fibers recruited by an electrode differs from the set that would normally be recruited in steady-state due to recent stimulation by other electrodes.

Studies have shown that lower electrode-to-modiolus distance is associated with better average outcomes, confirming the importance of ENI. Specifically, the study shows that when electrodes are positioned perimodiolarly (hugging the modiolus where the SG nerve cells are housed), they are associated with over 50 percentage points better word recognition rates than when the same electrode type is positioned distant to the modiolus in a retrospective study with almost 100 CI recipients. This shows that a substantial portion of the variability in outcomes with CIs can be attributed to a sub-optimal ENI.

One approach to improve outcomes and lower variability is to improve electrode design or surgical technique to achieve perimodiolar positioned electrodes. However, this will not address the over 500,000 individuals who have already been implanted, nor would it address newly implanted individuals who have sub-optimal neural health.

Another approach is to address sub-optimal ENI when the CI is programmed by selecting CI processor settings that account for the ENI. CIs are programmed by audiologists to determine stimulation settings. All CI manufacturers today use stimulation strategies based on the "continuous interleaved sampling" method. With this approach, sound frequency bands are assigned to stimulation channels, and channels are activated in a non-simultaneous, interleaved fashion in an attempt to avoid electric field interactions among channels. The programming task involves determining the number of stimulation channels and, for each stimulation channel, requires selecting the electrode configuration, signal levels, assigned sound frequency bands, and channel stimulation order. Electrode configuration defines which electrodes are active and which electrodes are used in each stimulation channel. In monopolar channel configuration, a single intra-cochlear electrode is used as a channel of stimulation with a distant extra-cochlear electrode serving as ground for return current. Multipolar configurations use multiple electrodes in a single stimulation channel. Minimum, maximum, and comfortable signal levels are chosen to optimize the volume of each channel. A frequency allocation table is determined to divide the sound frequency spectrum into bands and assign each stimulation channel one of those bands.

While CIs permit manipulation of very many settings that could address ENI, e.g., deactivation of electrodes that create overlapping excitation, the critical barrier exists in that there are no tools available to reliably estimate the patient-specific ENI. Decades of research in the CI community has been aimed at how to interpret available psychoacoustic (such as perceptual thresholds, i.e., the minimum levels of stimulation needed to sense a sound) and electrophysiological (such as recordings of electrically evoked compound action potentials) measurements that aim to interrogate the ENI. While these methods show promise, far field stimulation activates large groups of nerves and makes it difficult to estimate which fibers are activated by which electrodes. Further, all such measurements are a function not only of neural activation, but also of the path and resistance of tissues through which the current must pass to reach the nerves. As a result, it has not been possible to reliably extract and interpret the valuable information about the ENI contained in these metrics. Thus, audiologists must resort to a trial-and-error approach to determine settings, where weeks or months of experience with given settings are required before outcomes can be measured reliably. Convergence of the clinical adjustment process results in sub-optimal settings for most recipients and often requires many mapping sessions (typically 5-7 sessions/year for the first year and 1-2 per year thereafter at 1-2 hours per session, per ear) with an audiologist. Any advancement or tool that permits accelerating convergence to settings that better approximate natural fidelity could have significant impact for CI recipients, clinicians, and audiology centers.

As part of previous studies, the inventors have developed (R21DC012620) and clinically tested (R01DC014037, R01DC014462) tools that address a portion of ENI—reducing electrode stimulation overlap based on the distance from the electrodes to the sites where the nerves should be, assuming they are healthy. These tools rely on image processing techniques developed that make it possible, for the first time, to estimate the position of implanted CI electrodes relative to the SG sites in CT images, and thus to coarsely estimate the CI electrodes' neural stimulation patterns assuming the nerves are healthy, as is shown in FIG. 1D. These techniques open the door to the image-guided CI programming (IGCIP) techniques, which represent a new class of CI programming strategies in order to provide objective information that can assist audiologists with programming. The IGCIP strategy that has been the most successful is to deactivate electrodes that are estimated to create too much overlap with their neighbors, as estimated based on their distance to SG sites as demonstrated in FIG. 1D. In this case, electrodes 4 and 12 (shown in bold/italic in FIG. 1D) are found to have too much overlap due to distance to modiolus, and so they would be recommended for deactivation. Multiple publications have shown that this personalized IGCIP approach to programming results in statistically significant improvement in quantitative and subjective hearing performance in quiet and in noise on average. This is especially significant since few, if any, techniques have been developed in the past twenty years that have led to significant improvement in speech recognition scores with CIs through simple adjustment of stimulation settings. In particular, an over 5 percentage point increase in sentence recognition rates in difficult noisy conditions has been reported when IGCIP is implemented for 48 adults after only 4 weeks of use. Specifically, FIG. 2 shows the benefit of IGCIP, where (1) represents words, (2) represents sentences in a quiet environment, (3) represents sentences in a +10 dB environment, and (4) represents sentences in a +5 dB environment. As shown in FIG. 2, even greater benefit with IGCIP is seen when limiting to the adult demographic that is most likely able to quickly adapt quickly (N=65 individuals with post-lingual hearing loss and <1.5 years use of their CI), with median word and sentence recognition rates in quiet and in noise improving by nearly 10%. This is unsurprising, given that 4 weeks is likely not long enough of a learning period for drastic changes to the sensory input for many individuals. For example, longitudinal CI studies show speech recognition does not stabilize until 0.5-1 year after initial programming, and reprogramming studies show individuals with long-term use of specific settings are biased against changes. Despite this bias, the inventors have tested IGCIP on a total of 241 adults to this point without experience or language criteria and have found that 66% choose to keep IGCIP settings over their long-term clinical map. The inventors have also tested IGCIP in the pediatric population, where neural plasticity should be greatest. The study reported significant speech recognition benefit after 4 weeks of adaptation, and the subjects preferred the IGCIP map to their previous one in 18 of 21 experiments, which is a higher rate than in the adult population. However, while IGCIP leads to significant improvement on average, it does not lead to improvements for everyone, and it is hypothesized that this is because IGCIP, lacking any tool to measure neural health, assumes all the nerve fibers are healthy. In reality, post-mortem histological studies show that neural health is highly variable across individuals experiencing HL. Thus, for many individuals, IGCIP may recommend deactivating electrodes that are closer to healthy nerves than other electrodes that are left active, which could lead to performance declines. This could also explain in part why better results are achieved with pediatrics, as there is evidence that neural health is generally better in the pediatric CI population, and thus ignoring neural health for pediatrics is not detrimental as often as in adults. In addition to neural health, neural stimulation patterns of the electrodes are estimated in a coarse manner using only the distance from each electrode to the neural activation sites in the current IGCIP implementation, and the distance-based approximation to neural activation is over-simplified. This is because studies where neural activation models have been created using ex vivo histology/µCT imaging have shown the peak activation regions are often not in the closest nerves due to the indirect the path electric current takes through the cochlea as a function of tissue resistance and shape. However, even though IGCIP provides only a coarse estimate of ENI, the statistically significant average (and in some cases dramatic) improvement facilitated by IGCIP demonstrates that even partially accounting for the ENI does improve outcomes with CIs and supports that methods that more fully account for the ENI have a high likelihood to lead to even better, more consistent performance improvements. Nevertheless, it is possible that the method could be improved with a better estimate of the electrodes' neural activation patterns with a physics-based model.

Thus, one of the objectives of the present invention is to develop and validate a patient-personalized model-based CI programming (MOCIP) system and test new model-based programming strategies. In particular, the inventors propose developing tools that will permit comprehensively estimating the ENI and testing programming strategies that account for the ENI to improve CI performance. The potential impact of this technology is significant. It is estimated that less than 10% of the >1M individuals in the U.S. experiencing SP HL who could benefit from a CI pursue implantation, in part due to variable outcomes—interviews done with hearing-aid audiologists around the U.S. have revealed that hearing aid audiologists tend to only make their patients aware of CI as a last resort, specifically because of the perceived high-degree of uncertainty in outcomes with CIs. Reducing variability and improving outcomes with CIs could thus not only significantly impact quality of life for those who are currently receiving CIs, it could also lead to broader use and significant socioeconomic impact. High performing CI users (top 50% of individuals who receive a CI) achieve word recognition rates >60%, similar to individuals experiencing only moderate HL. An annual income per household difference of $10K or more has been shown between households with individuals experiencing moderate and SP HL. Specifically, the inventors introduce image processing and patient-specific anatomical modeling techniques that permit estimating the health of nerve bundles and which nerve fiber bundles each electrode recruits. Using this information, it is possible to determine patient-specific stimulation settings by MOCIP, which account for the individual's ENI and lead to improved hearing outcomes.

Certain aspects of the present invention relates to systems and methods for performing MOCIP on a patient-customized ENI model. FIG. 3 schematically shows a system for performing MOCIP on a patient-customized ENI model according to one embodiment of the invention. Specifically, the system 300 is in the form of a computing device, which may be a general computer or a specialized computer in communication with or including the externally-worn processor of the CI. As shown in FIG. 3, the system 300 includes a processor 310, a memory 320, and a storage device 330, and a bus 340 interconnecting the processor 310, the memory 320 and the storage device 330. In certain embodiments, the computing device of the system 300 may include necessary hardware and/or software components (not shown) to perform its corresponding tasks. Examples of these hardware and/or software components may include, but not limited to, other required memory modules, interfaces, buses, Input/Output (I/O) modules and peripheral devices, and details thereof are not elaborated herein.

The processor 310 controls operation of the system 300, which may be used to execute any computer executable code or instructions. In certain embodiments, the processor 310 may be a central processing unit (CPU), and the computer executable code or instructions being executed by the processor 310 may include applications, codes or instructions stored in the computing device of the system 300. In certain embodiments, the computing device of the system 300 may run on multiple processors, which may include any suitable number of processors.

The memory 320 may be a volatile memory module, such as the random-access memory (RAM), for storing the data and information during the operation of the computing device of the system 300. In certain embodiments, the memory 320 may be in the form of a volatile memory array. In certain embodiments, the computing device of the system 300 may run on more than one memory 320.

The storage device 330 is a non-volatile storage media or device for storing the computer executable code, such as an operating system (OS) and the software applications for the computing device of the system 300. Examples of the storage device 330 may include flash memory, memory cards, USB drives, or other types of non-volatile storage devices such as hard drives, floppy disks, optical drives, or any other types of data storage devices. In certain embodiments, the computing device of the system 300 may have more than one storage device 330, and the software applications of the computing device of the system 300 may be stored in the more than one storage device 330 separately.

As shown in FIG. 3, the computer executable code stored in the storage device 230 may include a MOCIP module 350. Specifically, the MOCIP module 350 is a software module which, when executed, causes the processor 310 to perform MOCIP on a patient-customized ENI model. Details of the methods and processes related to MOCIP are hereinafter elaborated with reference to the flowcharts as shown in FIGS. 4A-4H. In certain embodiments, the methods and processes as shown in FIGS. 4A-4H may be implemented on the system as shown in FIG. 3. It should be particularly noted that, unless otherwise stated in the present disclosure, the steps of the methods and processes may be arranged in a different sequential order, and are thus not limited to the sequential order as shown in FIGS. 4A-4H.

Figure 4A:
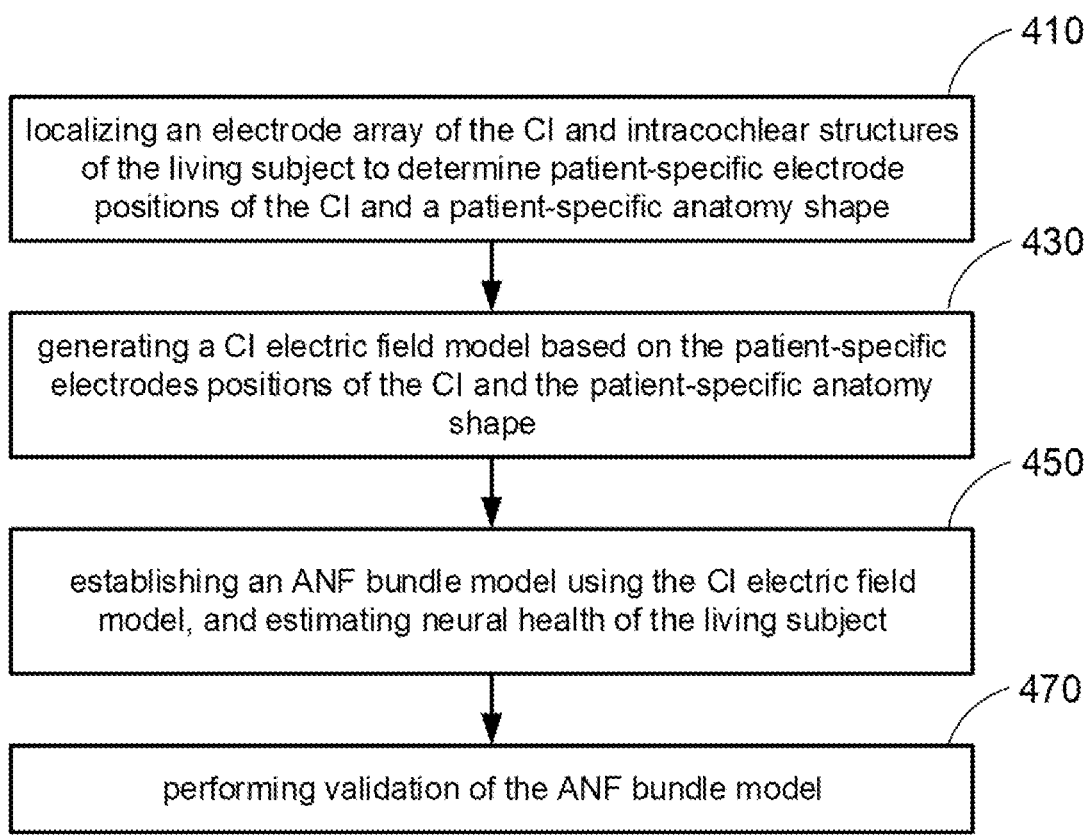
FIG. 4A shows a flowchart of a method for performing MOCIP on a living subject with a CI to determine stimulation settings of the patient-customized ENI model according to one embodiment of the invention.

FIG. 4A shows a flowchart of a method for performing MOCIP on a living subject with a CI to determine stimulation settings of the patient-customized ENI model according to one embodiment of the invention. Specifically, as shown in FIG. 4A, at procedure 410, an electrode array of a cochlear implant (CI) implanted on a living subject (i.e., a patient) and intracochlear structures of the living subject are localized in order to determine patient-specific electrode positions of the CI and a patient-specific anatomy shape. Then, at procedure 430, a CI electric field model is generated based on the patient-specific electrodes positions of the CI and the patient-specific anatomy shape. Then, at procedure 450, an ANF bundle model is established using the CI electric field model, and neural health of the living subject may be estimated using the ANF bundle model. Optionally, at procedure 470, validation of the ANF bundle model may be performed.

Figure 4B:
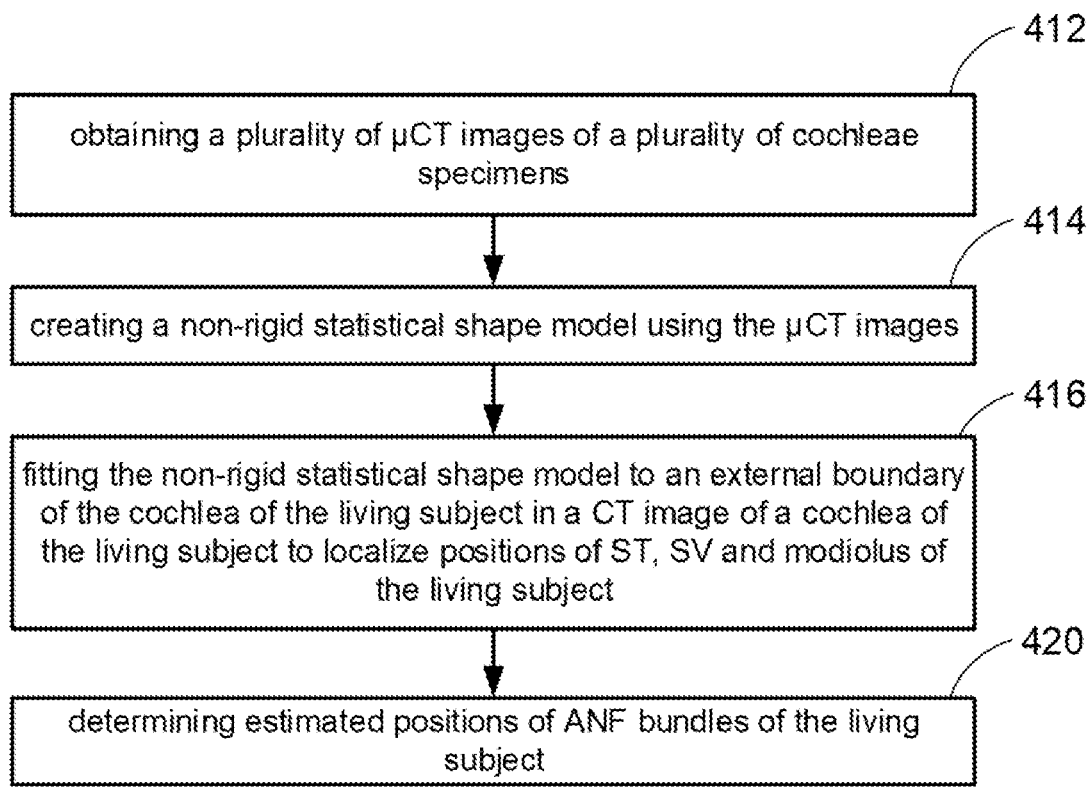
FIG. 4B shows a flowchart of the process for determining the patient-specific anatomy shape according to one embodiment of the invention.
Figure 4C:
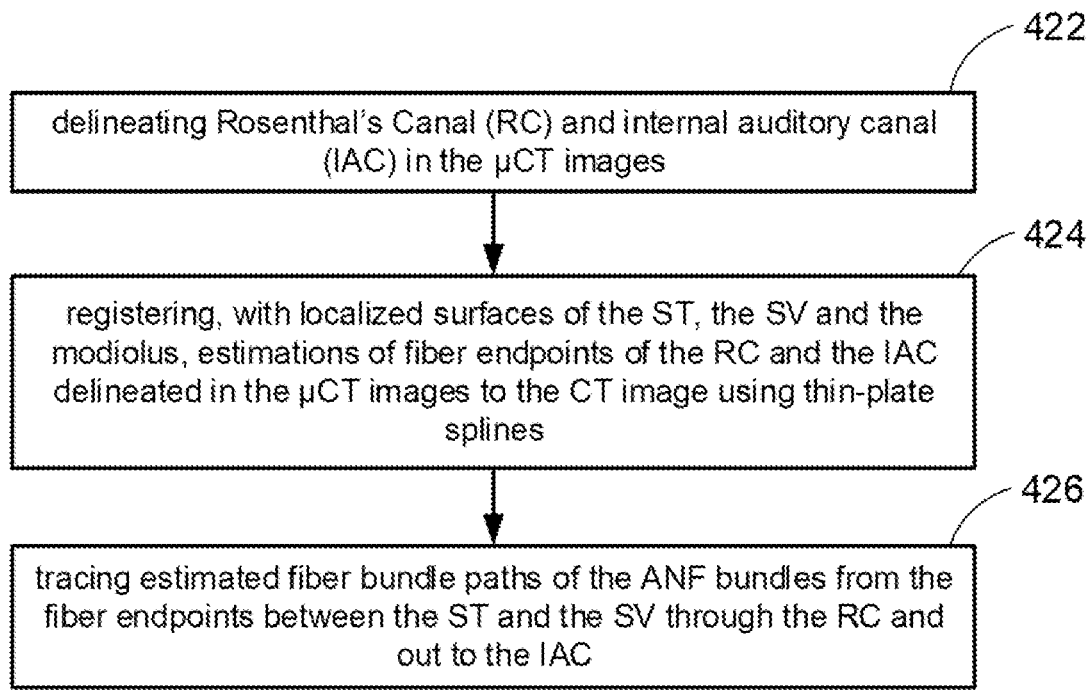
FIG. 4C shows a flowchart of the process for determining estimated positions of the ANF bundles according to one embodiment of the invention.

FIG. 4B shows a flowchart of the process for determining the patient-specific anatomy shape (see procedure 410 in FIG. 4A) according to one embodiment of the invention. As shown in FIG. 4B, at procedure 412, multiple micro computed tomography (μCT) images of a plurality of cochleae specimens are obtained ex vivo. At procedure 414, a non-rigid statistical shape model is created using the μCT images. Once the non-rigid statistical shape model is created, at procedure 416, a fitting action is performed to fit the non-rigid statistical shape model to an external boundary of the cochlea of the living subject in a CT image of a cochlea of the living subject to localize positions of visible structures, such as scala tympani (ST), scala vestibuli (SV) and modiolus of the living subject. Then, at procedure 420, estimated positions of invisible structures such as ANF bundles of the living subject are determined. FIG. 4C shows a flowchart of the detailed process for determining estimated positions of the ANF bundles according to one embodiment of the invention. As shown in FIG. 4C, at procedure 422, the μCT images are processed to delineate Rosenthal's Canal (RC) and internal auditory canal (IAC) in the μCT images. Then, at procedure 424, estimations of fiber endpoints of the RC and the IAC delineated in the μCT images are registered to the CT image with localized surfaces of the ST, the SV and the modiolus using thin-plate splines. Finally, at procedure 426, estimated fiber bundle paths of the ANF bundles can be traced from the fiber endpoints between the ST and the SV through the RC and out to the IAC.

Figure 4D:
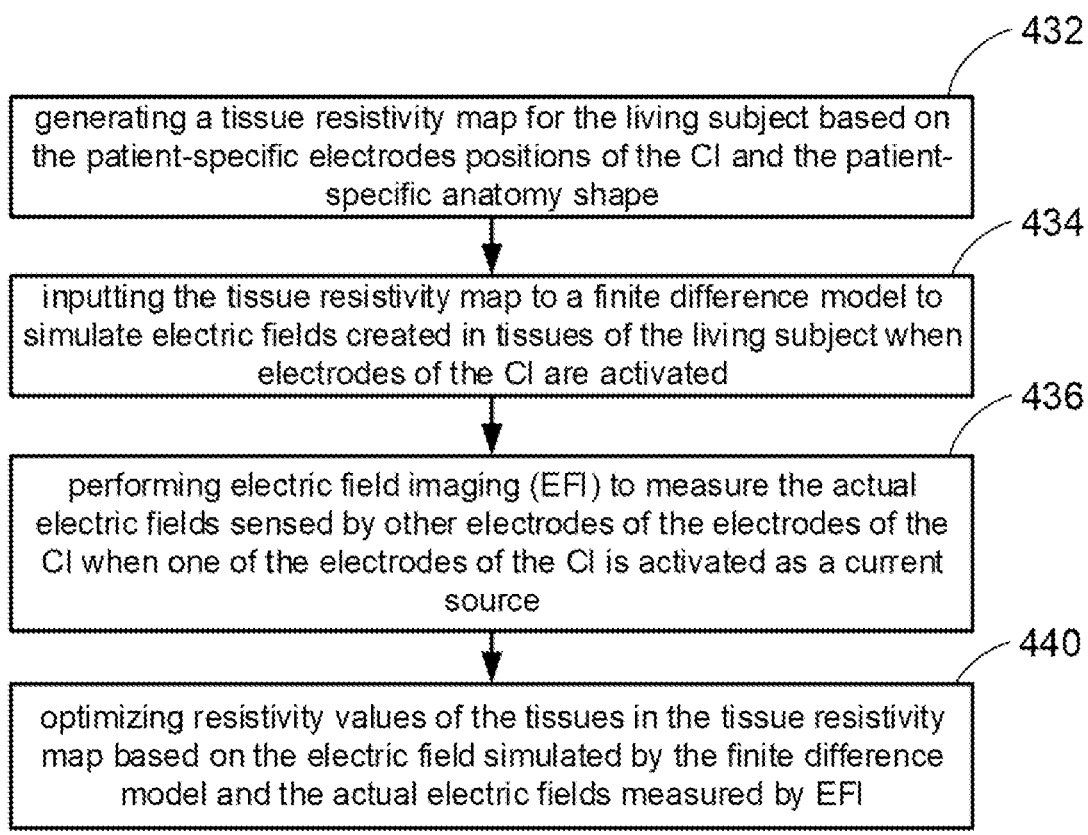
FIG. 4D shows a flowchart of the process for generating the CI electric field model according to one embodiment of the invention.
Figure 4E:
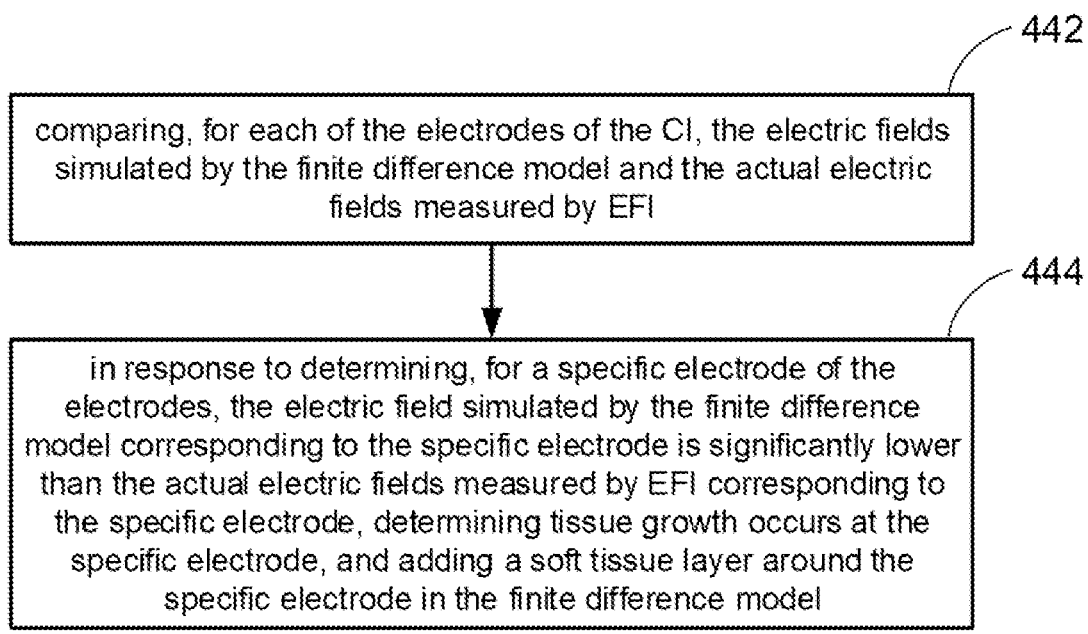
FIG. 4E shows a flowchart of the process for optimizing the resistivity values of the tissues according to one embodiment of the invention.

FIG. 4D shows a flowchart of the process for generating the CI electric field model (see procedure 430 in FIG. 4A) according to one embodiment of the invention. As shown in FIG. 4D, at procedure 432, a tissue resistivity map for the living subject is generated based on the patient-specific electrodes positions of the CI and the patient-specific anatomy shape. Then, at procedure 434, the tissue resistivity map is used as input to a finite difference model to simulate electric fields created in tissues of the living subject when electrodes of the CI are activated. At procedure 436, electric field imaging (EFI) is performed to measure the actual electric fields sensed by other electrodes of the electrodes of the CI when one of the electrodes of the CI is activated as a current source. Finally, at procedure 440, optimization for the resistivity values of the tissues in the tissue resistivity map is performed based on the electric field simulated by the finite difference model and the actual electric fields measured by EFI. FIG. 4E shows a flowchart of the process for optimizing the resistivity values of the tissues according to one embodiment of the invention. As shown in FIG. 4E, at procedure 442, comparison is performed for each of the electrodes of the CI to compare the electric fields simulated by the finite difference model and the actual electric fields measured by EFI. In this case, it is possible that, for some of the electrodes, the electric field simulated by the finite difference model corresponding to the electrode is significantly lower than the actual electric fields measured by EFI corresponding to the electrode. At procedure 444, in response to determining, for a specific electrode, the electric field simulated by the finite difference model corresponding to the specific electrode is significantly lower than the actual electric fields measured by EFI corresponding to the specific electrode, tissue growth is deemed to have occurred at the specific electrode, and thus, a soft tissue layer is added around the specific electrode in the finite difference model.

Figure 4F:
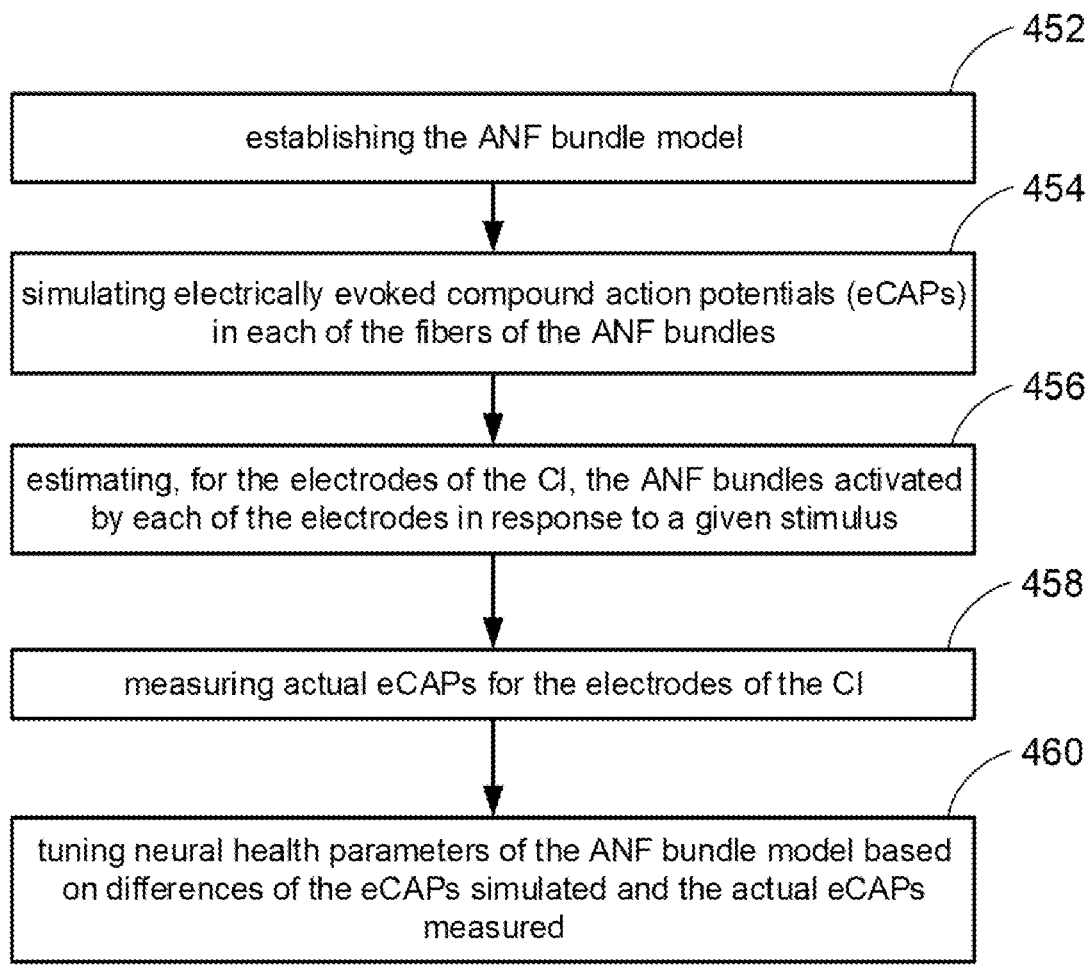
FIG. 4F shows a flowchart of the process for estimating the neural health of the living subject according to one embodiment of the invention.

FIG. 4F shows a flowchart of the process for estimating the neural health of the living subject (see procedure 450 in FIG. 4A) according to one embodiment of the invention. As shown in FIG. 4F, at procedure 452, the ANF bundle model is established with a plurality of ANF bundles, and each of the ANF bundles includes a plurality of fibers. At procedure 454, a simulation is performed to simulate or estimate electrically evoked compound action potentials (eCAPs) in each of the fibers of the ANF bundles. At procedure 456, estimation is performed for the electrodes of the CI to estimate the ANF bundles activated by each of the electrodes in response to a given stimulus. Optionally, at procedure 458, actual eCAPs for the electrodes of the CI are measured, and at procedure 460, tuning of neural health parameters of the ANF bundle model is performed based on differences of the eCAPs simulated and the actual eCAPs measured.

Figure 4G:
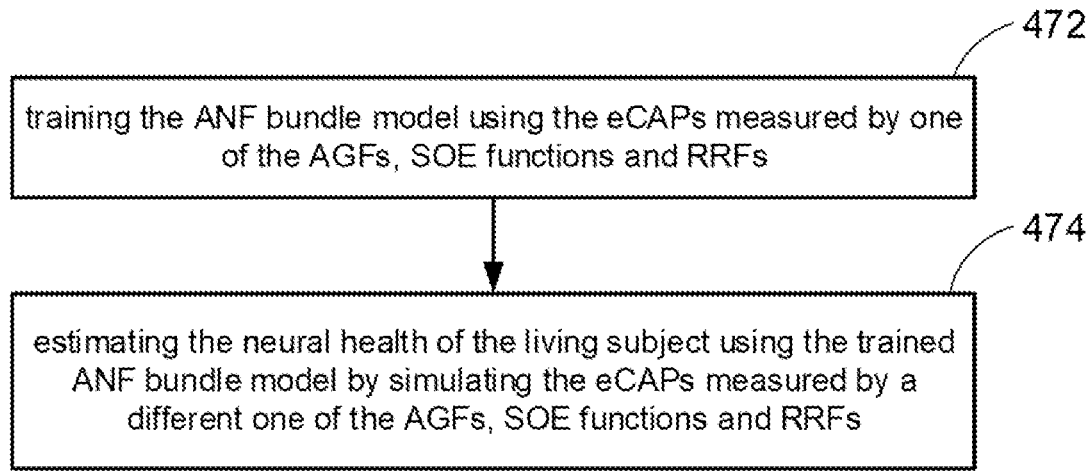
FIG. 4G shows a flowchart of the process for performing validation of the ANF bundle model according to one embodiment of the invention.
Figure 4H:
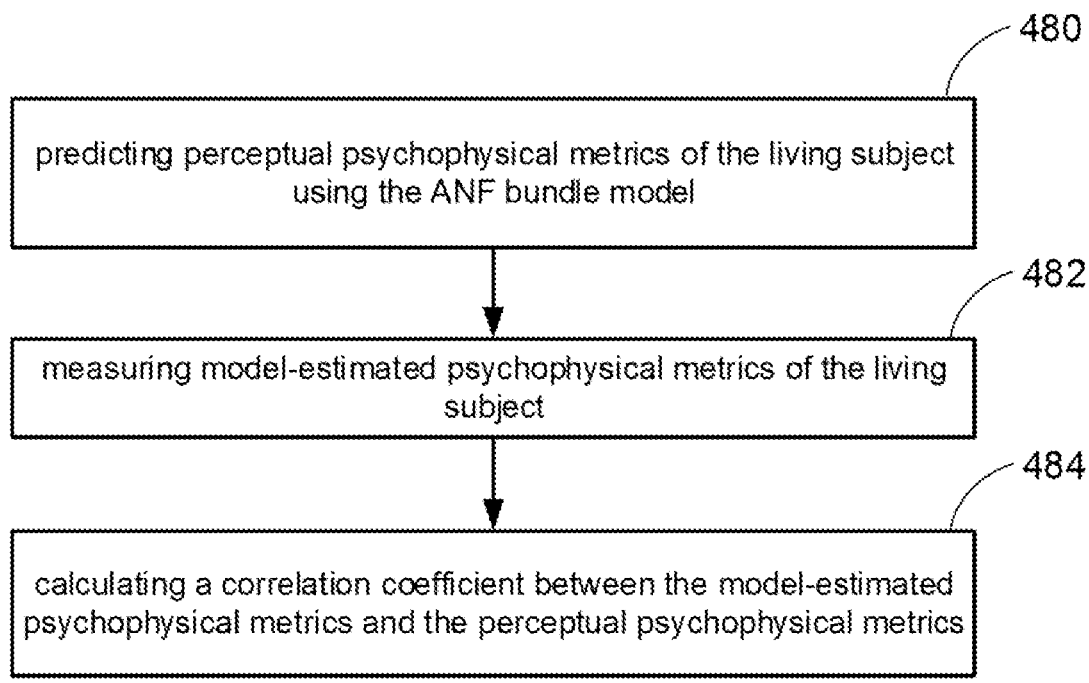
FIG. 4H shows a flowchart of the process for performing validation of the ANF bundle model according to another embodiment of the invention.

FIGS. 4G and 4H show flowchart of the process for performing validation of the ANF bundle model according to certain embodiments of the invention. As shown in FIG. 4G, at procedure 472, validation of the ANF bundle model may be performed by training the ANF bundle model using the eCAPs measured by one of the AGFs, SOE functions and RRFs. Then, at procedure 474, the trained ANF bundle model is used to estimate the neural health of the living subject by simulating the eCAPs measured by a different one of the AGFs, SOE functions and RRFs. Alternatively, as shown in FIG. 4H, at procedure 480, validation of the ANF bundle model may be performed by predicting perceptual psychophysical metrics of the living subject using the ANF bundle model. Then, at procedure 482, corresponding model-estimated psychophysical metrics of the living subject are measured. Thus, at procedure 484, a correlation coefficient between the model-estimated psychophysical metrics and the perceptual psychophysical metrics may be calculated for validation.

In yet another aspect of the present invention, a non-transitory tangible computer-readable medium is provided for storing computer executable instructions which, when executed by one or more processors, cause the method for performing MOCIP on a living subject with a CI to determine stimulation settings of a patient-customized ENI model as described above to be performed. The storage medium/memory may include, but is not limited to, high-speed random access medium/memory such as DRAM, SRAM, DDR RAM or other random access solid state memory devices, and non-volatile memory such as one or more magnetic disk storage devices, optical disk storage devices, flash memory devices, or other non-volatile solid state storage devices.

MOCIP could significantly improve outcomes for current CI recipients, but also has the potential to lead to a paradigm shift in the way CIs of the future are designed. In order to show that the MOCIP techniques of the present invention may be more effective than the current strategies employed in the CIs, the inventors have conducted the following experiments designed to measure the benefit of MOCIP techniques. Details of the experiments are described below.

Experiment One

Certain embodiments of the systems and methods are tested using patient-customized, image-based computational models of ANF stimulation of the electrically stimulated cochlea which allow estimation of intra-cochlear electric fields (EF) created by the CI for individual patients. Further, it is proposed to use these EF models as input to ANF activation models to predict neural activation caused by electrical stimulation with the CI.

The ANF stimulation models are built on three critical components: the biological auditory nerve model proposed by Rattay et al., the CT-based high-resolution EAM of the electrically stimulated cochlea, and the auditory nerve fiber segmentation. Details of how these models help to describe auditory nerves from biological, electrical, and spatial features respectively, as well as the approach to combine these models and build the novel, health-dependent ANF stimulation models based on them will be hereinafter elaborated.

Biological Nerve Model

Figure 5:
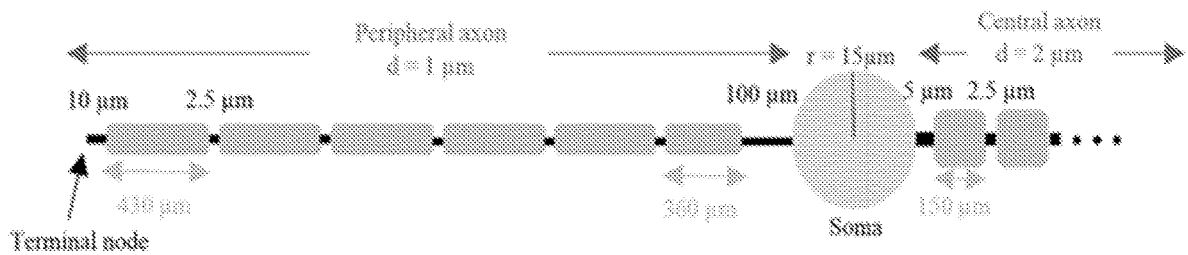
FIG. 5 schematically shows geometry of an ANF simulation and activation model according to one embodiment of the invention.

FIG. 5 schematically shows geometry of an ANF simulation and activation model according to one embodiment of the invention. The model proposed in by Rattay et al. introduce three major features that differs from other nerve models. First, they use compartment model which includes several subunits with individual geometric and electric parameters as shown in FIG. 5. Second, Ion channel dynamics are described by a modified Hodgkin-Huxley (HH) model, namely, the 'warmed' HH (wHH) model. The wHH includes sodium, potassium and leakage currents and has the following form:

$$\frac{dV}{dt} = [-g_{Na}m^3h(V-V_{Na}) - g_Kn^4(V-V_K) - g_L(V-V_L) + i_{stimulus}]/c \quad (1)$$

$$\frac{dm}{dt} = [-(\alpha_m + \beta_m)m + \alpha_m]k \quad (2)$$

$$\frac{dh}{dt} = [-(\alpha_h + \beta_h)h + \alpha_h]k \quad (3)$$

$$\frac{dn}{dt} = [-(\alpha_n + \beta_n)n + \alpha_n]k \quad (4)$$

$$k = 3^{T-6.3} \quad (5)$$

$$V = V_i - V_e - V_{rest} \quad (6)$$

where V, $V_i$, $V_e$ and $V_{rest}$ are the membrane, internal, external and resting voltages, and $V_{Na}$, $V_K$, and $V_L$ are the sodium, potassium and leakage battery voltages, respectively. $g_{Na}$, $g_K$, $g_L$ are the maximum conductance and m, h, n are probabilities with which the maximum conductance is reduced with respect to measured gating data, for sodium, potassium, and leakage, respectively. $i_{stimulus}$ is the current produced by electrode stimulation, and c is the membrane capacity. Finally, $\alpha$ and $\beta$ are voltage dependent variables that were fitted from measured data, k is the temperature coefficient, and T is temperature in Celsius. With wHH, the gating processes are accelerated (m, h, n are multiplied by 12), which best fit to observed temporal behavior of human auditory nerves compared to the original HH model, and leakage conductances are multiplied by the factor 10 to simulate 10-fold channel density. Also, the influence of membrane noise is also taken into account in their approach. These features allow the model to simulate the electrically excited auditory nerves in the human cochlea more accurately than models based on animals.

Electro-Anatomical Model and ANF Segmentation

The inventors has created CT-based high-resolution EAMs to determine the patient-specific EF caused by the current injected via CI electrodes. Briefly, this EAM estimates a volumetric map of the EF through the cochlea created by the CI. The EAM is customized for each patient by customizing a conductivity map so that estimated impedances between all combinations of the CI electrodes best match clinical measurements of these quantities, which are termed Electrical Field Imaging (EFI). Then, the EF can be found by solving Poisson's equation for electrostatics, which is given by $\nabla \cdot J = -\sigma \nabla^2 \Phi$, where $\Phi$ is the EF, J is the electric current density and $\sigma$ is the conductivity. The inventors are able to define the current source and ground for the CI versus other nodes by manipulating the left-hand side of the equation. The tissue in this model was assumed to be purely resistive, thus the amount of current enters a node equals to the amount of current that leaves the same node. The finite difference method solution to it can be found by solving $A\vec{\Phi} = \vec{b}$, where A is a sparse matrix containing coefficients of the linear sum of currents equations, $\vec{\Phi}$ are the set of node voltages that are being determined and are concatenated into a vector, and b(i) equals to +1 µA if the ith node is a current source and 0 otherwise. The nodes representing ground are eliminated from the system of linear equations, so the net current is not constrained for those nodes. This system of linear equations is then solved by using the bi-conjugate gradient method.

Figure 6:
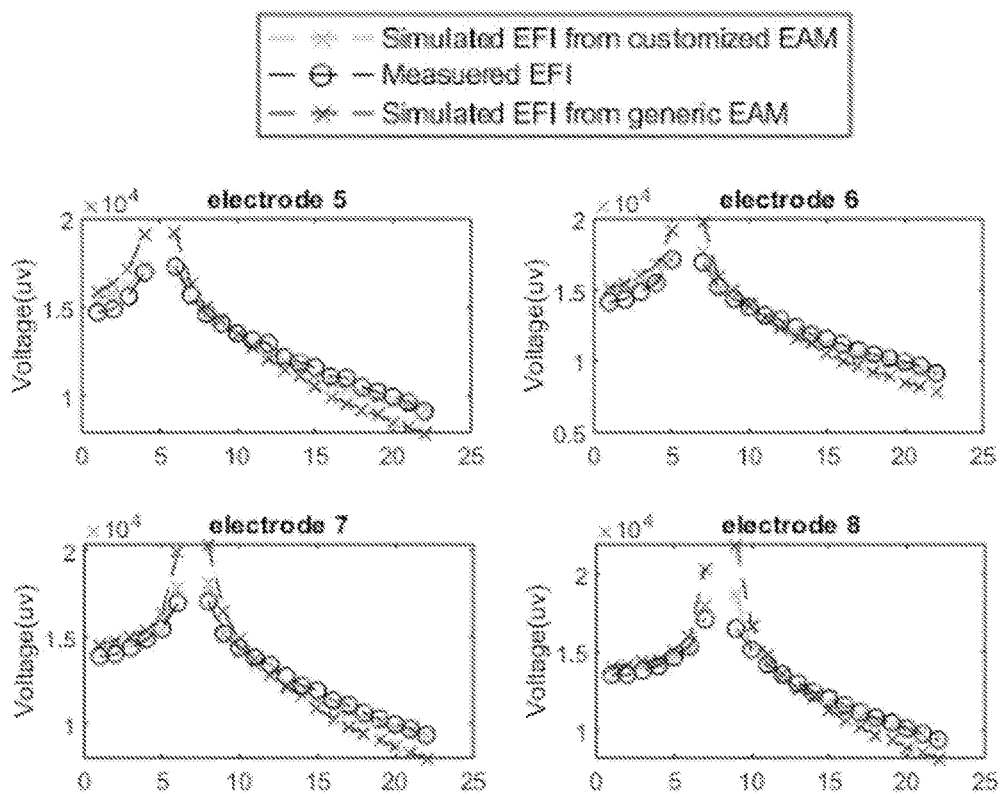
FIG. 6 shows electrical field imaging (EFI) simulation of a customized electro-anatomical model (EAM) and a generic EAM according to certain embodiments of the invention.

The EAMs may be electrically customized by optimizing the tissue resistivity estimates to minimize the average error between simulated EFIs and measured EFIs. The resistivity values for different tissue classes, including electrolytic fluid, soft tissues, neural tissue, and bone, are bound to vary in a range of 50 to 150% of their default values, which are 300, 50, 600, and 5000 Ωcm respectively. FIG. 6 shows the EFI simulation of a customized EAM and a generic EAM which uses default electrical properties for 4 electrodes of the same subject, demonstrating much better agreement between simulated and measured EFI after customizing electrical properties.

Figure 7:
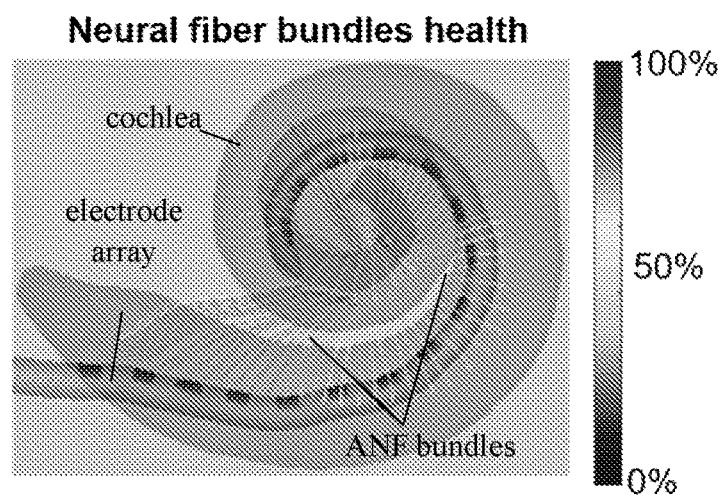
FIG. 7 shows the spatial distribution of ANF bundles with a nerve health estimate according to one embodiment of the invention.

To localize the ANFs, the inventors use a semi-automatic segmentation technique. This approach relies on prior knowledge of the morphology of the fibers to estimate their position. It treats the fiber localization problem as a path-finding problem. Several points are automatically defined as landmarks using the segmentation of the cochlea. Paths representing 75 fiber bundles that are evenly spaced along the length of the cochlea are then constructed by graph search techniques that gives the shortest path connecting all the landmarks. Because the paths are computed independently and in close proximity, sometimes they overlap or cross. As a post-processing step, manual edits to some of the paths are required. Example results of this process are shown in FIG. 7.

Method

There are approximately 30,000 ANFs in a healthy human cochlea. These ANFs are represented using auditory nerve bundles that are segmented along the length of the cochlea as shown in FIG. 7. To reduce the computational cost of our approach, only 75 distinct bundles are represented, and each represents potentially hundreds of fibers. The proposed nerve bundle action potential model is $P_M HM + P_U H(1-M)$, where $P_M$ and $P_U$ are the action potential responses of single ANF cell biological nerve models as described above for a myelinated fiber and the degenerated, unmyelinated fiber model, respectively. H is the number of living fibers in the bundle that can be recruited for stimulation. M is the fraction, among those ANFs, of healthy versus degenerated ones. Thus, the bundle action potential is the superposition of the two fiber model action potential predictions scaled by the number of such fibers to be present in the bundle. An approach to determine patient customized values for these two parameters for each of the 75 distinct bundles is described below.

The biological ANF model permits simulating action potentials (APs) created by ANFs as a result of the EF the ANF is subjected to. The EF sampled at discrete locations along the fiber bundle—each node of Ranvier (black nodes between myelinated segments in FIG. 7)—is used to drive the ANF activation model. The EF generated by the CI electrodes can drive the ANF models and can be estimated using our CT-based high-resolution EAM of the electrically stimulated cochlea as described above.

Next, the bundle model is used to simulate neural response measurements that can be clinically acquired. These measurements include recordings acquired using the CI electrodes of the combined AP signal that is created by the set of ANFs activated following a stimulation pulse created by the CI. Such measurements are called electrically evoked compound action potentials (eCAPs). Several eCAP-based functions can be clinically acquired. The most common are the amplitude growth function (AGF), which samples how the magnitude of recorded eCAPs (µV) grow as the current is increased for the stimulation pulse signal; and the spread of excitation (SOE) function, which measures the fraction of eCAP responses for two stimulating electrodes that are generated from the same ANFs. Both AGFs and SOEs can be simulated using our models and clinically measured using the patient's implant. While both AGF and SOE are rich with information about the electro-neural interface and have been acquirable for CI patients for decades, these metrics are not routinely used for clinical programming because they have been difficult to interpret. Thus, the method proposed provides a unique opportunity to (1) estimate neural health by tuning model neural health parameters so that model predicted eCAP functions match clinically measured ones; and (2) provide a physical explanation for the AGF and SOE measurements. Both of these typically unknown quantities could significantly improve an audiologist's ability to program the CI.

Then, neural health parameters for each ANF bundle are tuned so that simulated AGF functions for each electrode in the array best match the corresponding clinically measured ones. Finally, validation is performed to evaluate the health prediction by simulating SOE functions using the model with the estimated neural health parameters and compare the results to clinical measured SOE to demonstrate the predictive value of the proposed models. The following subsections detail each step of our approach.

Dataset

N=8 patients who had undergone CI surgery were used to create neural health estimation models. All the patients underwent pre- and post-implantation CT imaging needed to localize the intra-cochlear position of the electrodes and to create the tissue classification maps for the EAM models. The three clinical electrophysiological measurements critical for tuning and evaluating our models (EFI, AGF, and SOE) were also collected for all electrodes, for all patients with institutional review board approval.

Nerve Model

Each nerve fiber model follows the approach of Rattay et al. as described above, and the same electrical and geometrical properties as Rattay did are used. The modeling is done using the NEURON simulation environment. The overview of the auditory nerve fiber used is shown in FIG. 5. As shown in FIG. 5, each nerve model includes three subunits, which are the peripheral axon, the soma and the central axon. The peripheral axon is located near hair cells in a human cochlea. They are myelinated when the fiber is healthy and fully functional. It is also common in patients with hearing loss that fibers where the peripheral axon has become unmyelinated exist and could have a weaker response to stimulation. They are defined as functional but 'unhealthy' ANFs. Then it is possible to parameterize the health of each nerve bundle by varying the number of fibers, H, as well as the ratio of myelinated vs unmyelinated fibers, M, a for each ANF bundle.

The bundle model simulates bundle APs to the estimated EF generated by CI electrodes as previously discussed. Subsequently, eCAP measurements can be simulated in the model. To do this, each node of Ranvier for each bundle is treated as a current source, and the same finite difference method discussed above for estimating EF created by the CI is repurposed for estimating the EF created by the APs generated by all the bundles. This is done by defining bundle nodes as current sources corresponding to cross-membrane current. Thus, the result of each bundle model drives a new EAM to estimate the EF created by the ANFs in the cochlea. The value of the EF is then recorded at the site where the recording electrode is located. This process directly simulates the clinical eCAP measurement process.

In summary, the ECAP simulation can be divided into three steps: (1) for a given stimulating electrode, the EF is calculated using an EAM and record the resulting EF at the nodes of Ranvier for each nerve bundle; (2) the voltages are used as input to the neural activation models for both myelinated and unmyelinated nerves to compute the combined nerve bundle AP; and (3) the EF created by the bundle APs is estimated using another EAM, permitting simulated eCAP measurement from the position of recording electrode. In practice, in the final step, an EAM can be created independently for each bundle and the compound response at the recording electrode is then given by $$\text{simulated } eCAP = \sum_{i=1}^{75} P_{M,i} H_i M_i + P_{U,i} H_i (1 - M_i) \quad (8)$$

where $P_{M,i}$ and $P_{U,i}$ represent the value of the EF sampled at the recording electrode for the simulated eCAP of the myelinated and unmyelinated ANF model in the ith nerve bundle, respectively, and $H_i$ and $M_i$ are the number of fibers and fraction of those fibers that are healthy for the ith nerve bundle.

Optimization Process

Spoendlin et al. found that for a healthy human cochlea, the average number of fibers can vary between 500 fibers per millimeter (mm) to 1400 fiber per mm depending on the location within the cochlea. Given that a nerve bundle in our model can represent a region as wide as 0.4 mm, the boundary values for number of functional nerve fibers are set to be between 0 (all unresponsive) and 550 (all responsive) and the healthy ratio or the myelination ratio from 0 (all responsive nerve fibers are damaged) to 1.

Instead of determining values for $H_i$ and $M_i$ for each of the 75 nerve bundles independently, a set of control points are used to enforce spatial consistency in parameter values. Specifically, n+1 control points are defined along the length of cochlea, where n is the total number of active electrodes. The control points are positioned to bracket each electrode. The parameters at those control points were randomly initialized with $H_i$ between 0 to 550 and $M_i$ from 0 to 1. The parameters for each nerve bundle are then linearly interpolated along the length of the cochlea using the control points.

The bounded Nelder-Mead simplex optimization algorithm is used to optimize values at the control points. The cost function is calculated as the mean absolute difference between the simulated and measured AGF values for each electrode. Starting from a random initialization at each control point, the algorithm will iteratively calculate the parameters of every nerve bundle by interpolating control point values, simulate AGF using those parameters to evaluate the cost function discussed above, and determine new control point parameters using the Nelder-Mead simplex method until a maximum iteration number is reached or the change in error falls below the termination threshold (0.1 µV). The Algorithm pseudocode is presented in Algorithm 1.

---
Algorithm 1. Estimate the patient specific neural health parameters
---

Input: $P_{AGF}$ = Patient AGF measurement
Variables: $S_{AGF}$ = Simulated AGF data, H = Number of nerve fibers within bundles, M = Myelination ratio of fibers within bundles
Output: HC = Fiber count assigned to each control point, MC = Myelination ratio assigned to each control point
Start: Assign threshold and maxIteration, randomly assign HC and MC
While Δ|error|> threshold and counter < maxIteration
    Interpolate H and M using HC and MC
    Calculate $S_{AGF}$ using H and M
    For each electrode i
        $error_{AGF}$ [i] = mean(abs($P_{AGF}$ [i] − $S_{AGF}$ [i]))
    error = mean($error_{AGF}$)
    Optimize HC and MC using a constrained nonlinear search based on Nelder-Mead simplex

---

In the implementation, AGF values that were less than 35 µV were not included in the optimization process because low AGF values tend to be below the noise floor and are usually excluded from clinical analyses. During the experiments, Algorithm 1 is executed from 250 different random initializations for each patient model. The final fiber count and healthy ratio for every nerve bundle are determined as the median values across the 10 optimization runs that resulted in the lowest average error. This procedure diminishes the likelihood of choosing sub-optimal parameters that are local minima.

Results

The average absolute differences between the simulated and measured AGF and SOE values for fully customized EAMs are shown on the left side of Table 1.

TABLE 1

Average mean absolute difference between simulated and measured AGF and SOE.

| | Fully Customized Models | | | Generic Models | |
|---|---|---|---|---|---|
| Subject # | AGF error - before optimiz. health (µV) | AGF error - after optimiz. health (µV) | SOE error- testing error(µV) | AGF error - after optimiz. health(µV) | SOE error- testing error(µV) |
| 1 | 58 | 16 | 31 | 22 | 53 |
| 2 | 187 | 19 | 32 | 48 | 49 |
| 3 | 299 | 39 | 37 | 28 | 76 |
| 4 | 66 | 37 | 44 | 39 | 102 |
| 5 | 131 | 11 | 29 | 19 | 56 |
| 6 | 97 | 8 | 21 | 15 | 36 |
| 7 | 62 | 17 | 48 | — | — |
| 8 | 141 | 26 | 59 | — | — |
| Average | 134 | 21.6 | 39.5 | 28.5 | 62.0 |

The average absolute difference between the simulated and the measured AGF values could be interpreted as the training error. Mann-Whitney U tests reveal significant improvement in AGF errors after training (p<0.01). The error between the simulated and the measured SOE can be interpreted as the testing error since SOE was not used to optimize neural health parameters. Further, SOE is likely more sensitive to neural health than AGF because it is much more dependent on the spatial distribution of ANFs that contribute to the neural responses. The average SOE error across all patients after optimizing neural health parameters using our proposed method is 39.5 µV.

Figure 8A:
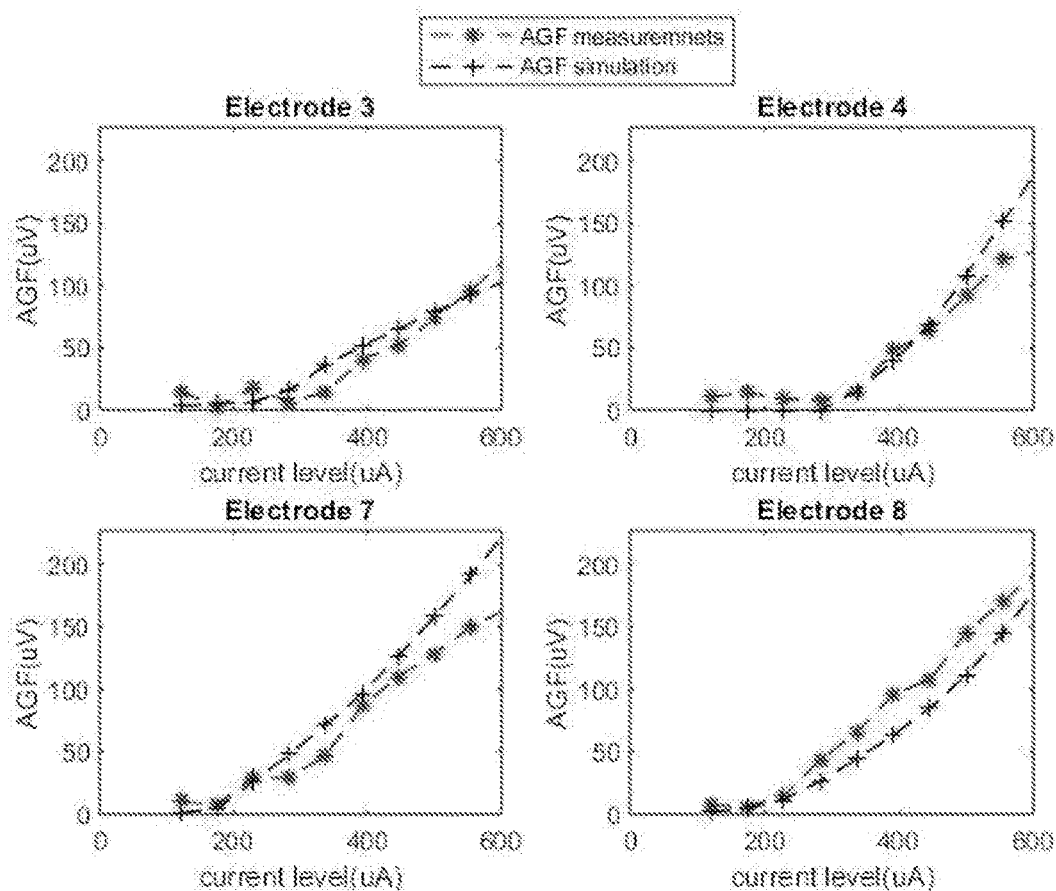
FIG. 8A shows comparison between measured and simulated amplitude growth function (AGF) data according to one embodiment of the invention.
Figure 8B:
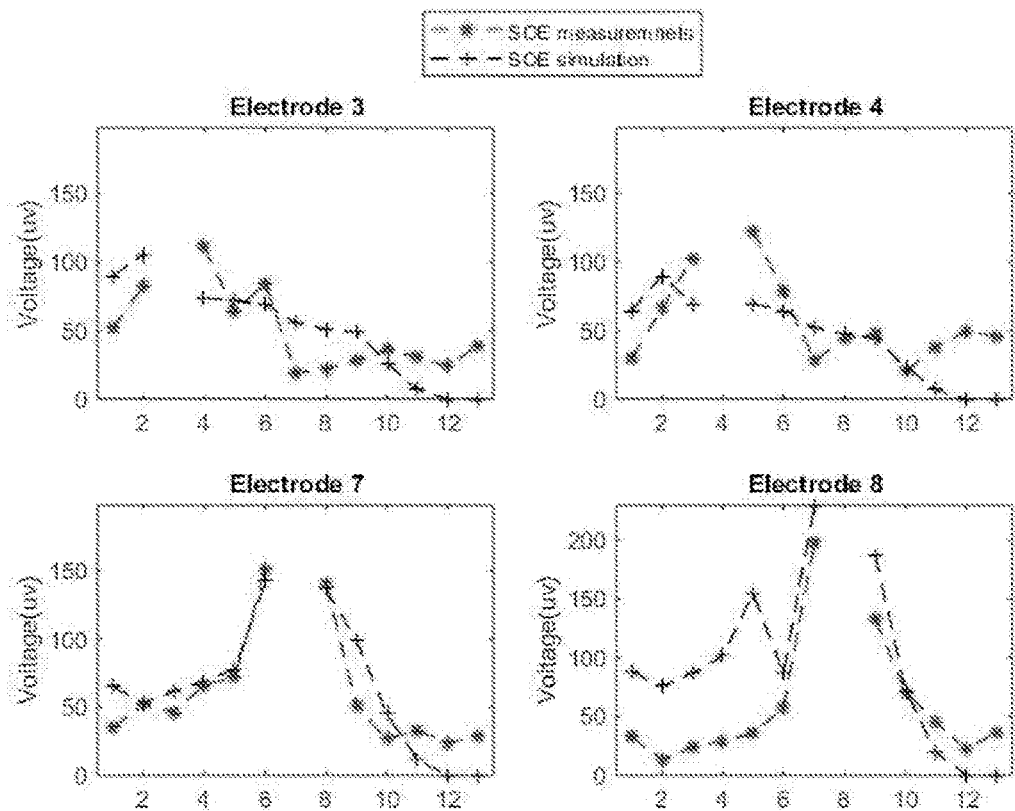
FIG. 8B shows comparison between measured and simulated spread of excitation (SOE) data according to one embodiment of the invention.
Figure 9:
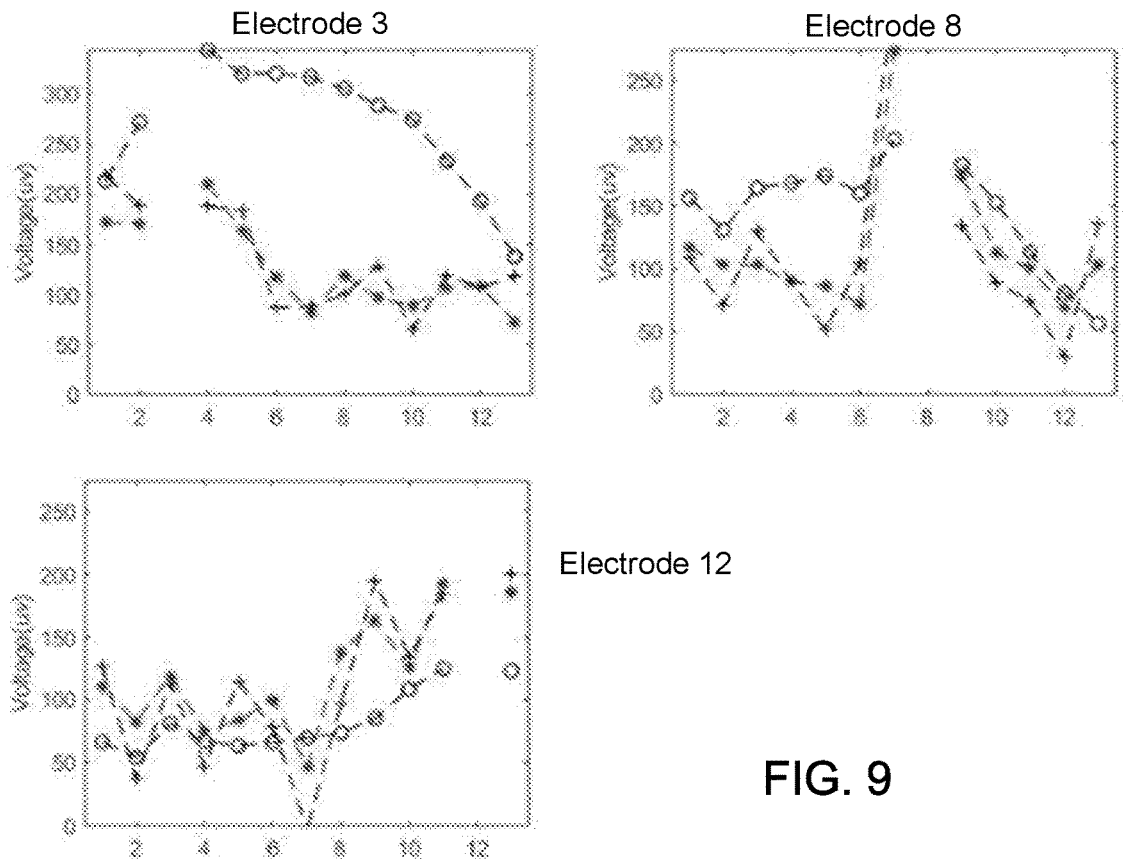
FIG. 9 shows SOE testing error for patient customized versus generic model according to one embodiment of the invention.

FIGS. 8A and 8B show comparison between measured and simulated AGF and SOE data for subject 1. Both of the quantitative and qualitative comparisons show excellent agreement between neural stimulation responses that are clinically measured and those that are predicted by our parameter optimized models. Further comparison is conducted for the difference between neural health estimation using our fully customized models vs. generic models, where default electrical properties are used, for the first 5 subjects in the right side of Table 1. The AGF error (training error) resulting from the generic and electrically customized models is similar while the testing error with fully customized models is much smaller than generic models. A one sided Mann-Whitney U test reveals significantly better (p<0.05) testing error with the fully customized model compared to the generic models. Example plots demonstrating the superiority of SOE simulations using customized for one subject (i.e., subject 4) are shown in FIG. 9. These results imply our patient-specific EAMs are critical, not only for EFI simulation, but also for accurate neural health estimation. An example neural health estimation result is shown in FIG. 7, where the neural health color-codes are a combined function of both health parameters equal to H (0.5+M). Varying health of several regions of nerves was identified by the proposed method in order for prediction to match measured AGF.

Experiment Two

Certain embodiments of the systems and methods are further tested with the hypothesis that complementing the IGCIP electrode position metrics, which ignore neural health, with electrophysiological measurements, which contain far field measurements of neural activation, will permit comprehensively estimating the ENI. To combine and interpret these sources of information, building upon the techniques developed in the previous project period, physics-based models are proposed to integrate the accurate localization of patient-specific electrode position developed for IGCIP and have neural health parameters that can be tuned such that model predictions match the electrophysiological measures. The result is a comprehensive, patient-specific model that offers, for the first time, (1) physical explanation of the electrophysiological measurements, which have been elusive to interpret, (2) estimation of the health of nerve fibers, and (3) estimation of the ENI, with the ability to simulate and predict neural activation for any type of stimulation. The modeling methods will enable estimation of the ENI with unprecedented detail, including estimating intra-cochlear tissue growth, fiber bundle-specific neural health, and localizing which healthy fibers are stimulated by which electrodes.

Figure 10:
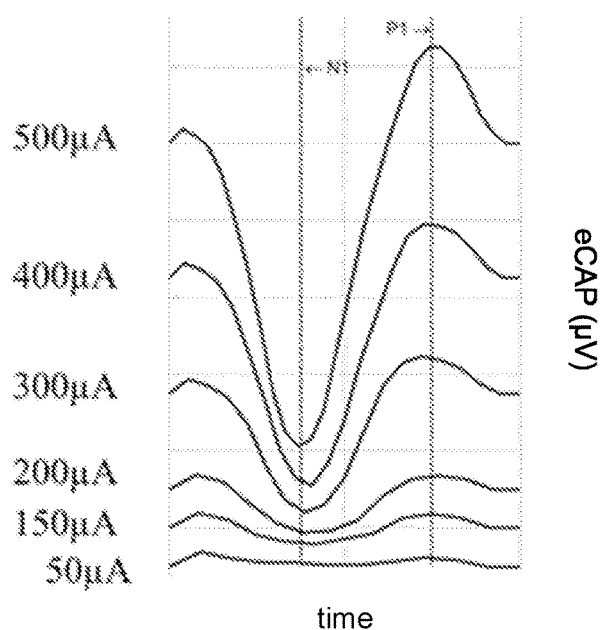
FIG. 10 shows an electrically evoked compound action potentials (eCAP) amplitude growth functions (AGF) stimulated by a patient-specific model according to one embodiment of the invention.
Figure 11A:
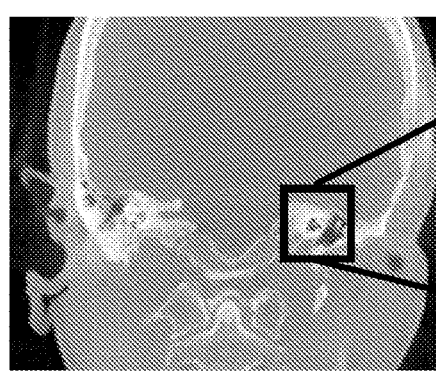
FIG. 11A shows (a) a CT image of a patient and (b) an enlarged image of the cochlea area according to one embodiment of the invention.
Figure 11A:
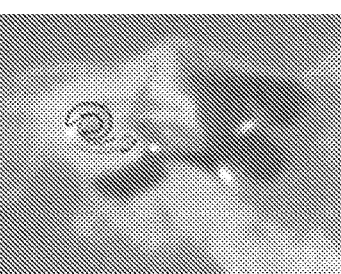
Figure 11B:
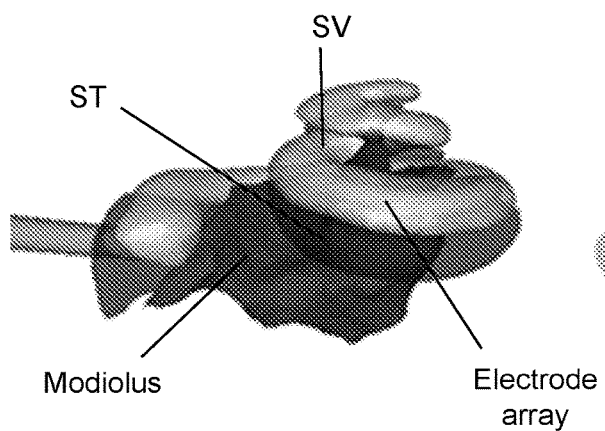
FIG. 11B shows localization of the ST, the SV, the modiolus and the electrode array of the CI according to one embodiment of the invention.
Figure 11C:
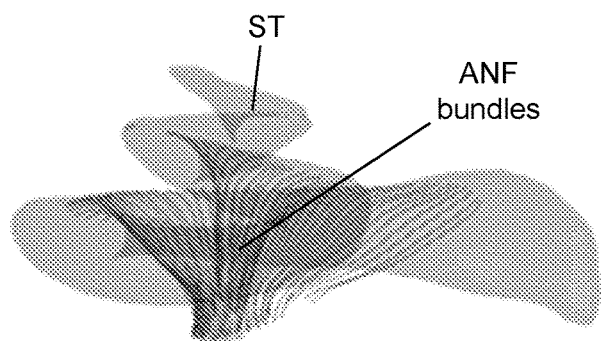
FIG. 11C shows localization of the ANF bundles according to one embodiment of the invention.

The electrophysiological measurements used are electrically evoked compound action potentials (eCAP), which is the far field recording by a CI electrode of the accumulated action potentials created of all fibers recruited by a stimulating electrode. The inventors propose to optimize neural health parameters, as well as stochastic fluctuation and gating parameters, using three eCAP-based measures: AGFs, SOE functions, and refractory recovery functions (RRF). FIG. 10 shows an electrically evoked compound action potentials (eCAP) AGF stimulated by a patient-specific model according to one embodiment of this invention. As shown in FIG. 10, the AGFs are measurements of the amplitude of eCAPs (P1-N1) recorded by the CI using an adjacent recording electrode when increasing current delivered to a stimulating electrode. SOE functions measure excitation overlap between contacts. Stimulation with a "masking" electrode puts the nerve fibers it recruits into a refractory state, during which another "probe" electrode can be activated. The difference between the eCAP measured for the probe electrode alone and the eCAP measured when the probe is "masked" by the masking electrode represents the amount of neural activation from fibers stimulated by both electrodes. SOE is the collection of eCAPs of all combinations of electrodes used as probes and maskers. The SOE eCAPs for one probe electrode while varying the masker across the array contain information regarding how wide of an activation region the probe creates. The RRF uses the same masking paradigm but the masker and probe are the same electrode and the masker-probe stimulus intervals are varied to assess the refractory recovery rate of the nerves being stimulated. As opposed to many psychophysical metrics that require subjective feedback from the patient, eCAP-based measurements are entirely objective. While they can require several minutes or hours to collect, they do not require the patient's attention and can even be done while still under anesthesia immediately after implantation. Despite these advantages, these promising metrics have been used surprisingly rarely for programming. The only widespread use has been for setting volume levels for populations that are unable to provide qualitative feedback to the audiologist, such as prelingual pediatrics. Since the eCAP measurements are a complex function of the health of a broad region of fibers as well as the paths and resistance of tissue through which the current travels, the inability to interpret these eCAP measurements has been a critical barrier for their use. However, by customizing our models such that they replicate eCAP measurements, our models provide a physical explanation for the eCAP measurements, and can offer clinicians an unprecedented direct estimation of the ENI.

Once an estimate of the ENI is obtained, it is possible to determine patient-specific stimulation settings, i.e., the MOCIP strategies, that account for the individual's ENI and lead to improved hearing outcomes. In this experiment, multiple MOCIP strategies were developed and tested, and the strategies are packaged into a tool that offers audiologists a set of patient-specific recommendations. These strategies and systems will lead to more efficient selection of CI program settings, and ultimately will lead to less variable and improved outcomes. Widespread use of such a tool would represent a paradigm shift in how CIs are programmed from a generic trial-and-error to a data driven, patient-personalized approach. MOCIP also has the potential to lead to a paradigm shift in the way CIs of the future are designed and operate, e.g., future CIs could permit stimulation strategies that adapt in real-time to account for the model-estimated refractory states of the fibers due to preceding stimulation in order to minimize channel interaction artifacts when they are expected, yet maximize signal fidelity when they are not.

The proposed modeling approach is summarized in three steps, including: (1) accurately localizing the electrode array and intracochlear structures using CT images and automatic algorithms, (2) creating a CI electric field model based on patient-specific electrode position and tissue resistivity, and (3) modeling auditory nerve fiber activation and estimate neural health. The resulting model can be used for patient-specific simulation of any stimulus.

Approach

The overall experiment goals were to (1) develop and test new IGCIP strategies and simultaneously (2) develop an automated approach for more comprehensive, physics-based modeling of current flow within the cochlea to improve upon the simplified approach used by IGCIP based purely on distance from the electrodes to the sites where the nerves should lie. The inventors recruited a total of 141 subjects for experiments. Participants were 54% female and 46% male; 2% Asian, 7% Black or African American, and 91% White. 1% of participants were Hispanic. The distribution of subjects roughly matches the distribution of CI recipients at Vanderbilt University. Subject selection was not based upon gender or race. No exclusion of any sex/gender/racial/ethnic group was performed. 29 of the participants were children.

The inventors have modified and tested IGCIP selection of electrodes to deactivate for use in different populations, including adults with prelingual HL, pediatrics, and combined electrical and acoustic stimulation patients with hearing preservation. The inventors have evaluated using IGCIP to determine frequency settings, including matching frequencies to the nerve characteristic frequencies as well as obtaining a better bilateral hearing match across ears, and developed a current steering settings selection method. Similarly to the initial deactivation strategy, these studies all showed improvement with IGCIP settings on average in speech recognition and/or subjective quality metrics, yet some subjects still show decline with IGCIP. The inventors have also developed a series of algorithms that automate the processes that enable IGCIP and allow clinically translation of IGCIP to make it more broadly available.

Simultaneously to developing and evaluating new IGCIP techniques, the inventors have worked towards more comprehensive models. The inventors have made significant progress towards developing more comprehensive patient-specific models of current flow in the cochlea, and developed automatic techniques for creating high resolution tissue resistivity maps that account for patient-specific anatomy shape, electrode position, and tissue electrical properties. The electric field created by the CI can be computed using these maps with finite difference models. However, it was found that estimating neural activation patterns using the electrode field alone was difficult as activation is a complex function of electric field shape. Thus, the inventors decided to augment the models with physics-based neural fiber activation models. First, methods were developed to localize the fibers. Next, with the ability to localize fibers, fiber activation models have been implemented, and initial tests of programming strategies were performed using the models as described below.

Anatomy & Electrode Localization

Figure 12:
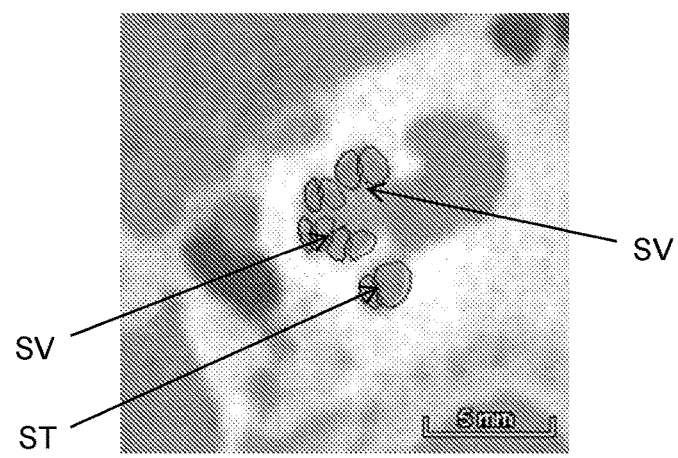
FIG. 12 shows a portion of a pre-operative CT image showing the ST and SV in a sagittal CT slice according to one embodiment of the invention.

To account for patient-specific anatomy and electrode position, the inventors rely on a suite of image processing algorithms developed to accurately and automatically localize the electrode position and anatomy shape. This includes the scala tympani (ST) and scala vestibuli (SV), the two main intra-cochlear cavities, as well as the modiolus and auditory nerve fiber bundles. Because the boundaries between these structures are too thin to be visible in conventional CTs (see arrows in FIG. 12 for example), direct localization in CT using standard image processing techniques is not possible. The inventors have developed a segmentation approach that uses a non-rigid statistical shape model created with micro CT ($\mu$CT) images, originally of 6 cochleae specimens, but has since been expanded to 16. Unlike CT, $\mu$CT cannot be applied in vivo due to radiation and space constraints, however, with ~1000× better volume resolution $\mu$CT enables imaging finer scale structures. These models are then automatically fitted to the external boundary of the patient cochlea that is visible in conventional CT and used to estimate the position of invisible portions of these structures. FIG. 12 shows a portion of a pre-operative CT scan and our segmentations presented as 2D contours. Using the same validation approach described with our original model with N=6 specimens, it was found that with the expanded dataset, average surface localization errors are reduced to 0.11 mm. Studies show that inter-subject variations are quantitatively substantial and clinically significant. However, it was found that models constructed with any combination of at least 8 of 16 specimens resulted in mean localization errors that were within 2.5% of those obtained with models constructed with 15 specimens when fitting the models to the CTs of remaining left-out specimens. In other words, 8 cochleae are enough to capture the range of population variance, and the 16 specimens used are more than adequate. This method has been successfully applied to images of more than 500 subjects in multiple studies aimed at investigating the relationship between electrode position and hearing outcomes.

Figure 13:
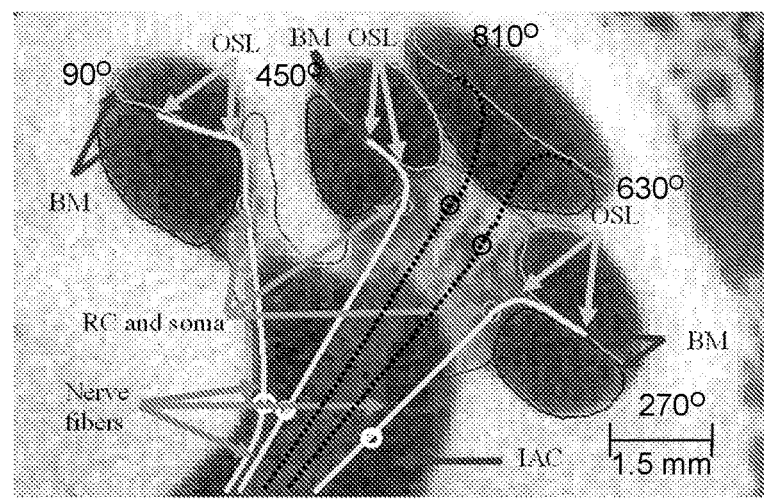
FIG. 13 shows a micro CT slice with contours around the ST, the SV, the modiolus, basilar membrane (BM), osseous spiral lamina (OSL), Rosenthal's Canal (RC), internal auditory canal (IAC), nerve fiber estimates, and the position of the soma in RC according to one embodiment of the invention.

A method has been developed to localize the auditory nerve fiber bundles. Specifically, the fibers are so fine that they are not directly visible in $\mu$CT, however, their locations relative to visible structures for segmentation are well known, as shown in FIG. 13. In particular, the fibers terminate between the ST and SV, proceed around the ST into Rosenthal's Canal (RC), and then proceed out into the internal auditory canal (IAC). Using the vertices that compose the ST, SV, and modiolus surfaces that were automatically localized as described above, it is possible to register estimations of the RC and IAC fiber endpoints delineated in $\mu$CT to new patient CT images using thin-plate splines. Finally, path finding techniques are used to trace 75 fiber bundle paths, each of which could contain up to 500 fibers, from their endpoints between the ST and SV through the RC and out to the IAC. Validation shows this process results in average fiber bundle localization errors under 0.2 mm.

Methods were also developed to automatically localize all currently available models of electrode arrays produced by the three FDA approved manufacturers. Specifically, the electrode array is composed of radiodense metal, and thus each electrode appears as a bright tube or series of bright blobs in CT. The methods aim to identify the center lines of the tube or blobs to localize the contacts, and studies using $\mu$CT for ground truth show the possibility to automatically localize each contact with average errors ~0.1 mm.

CI Electric Field Models

Figure 14A:
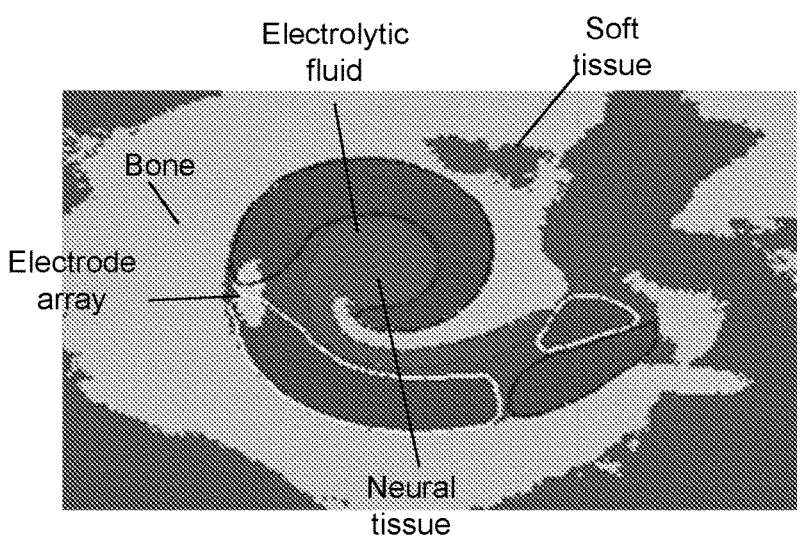
FIG. 14A shows a slice of 3D tissue resistivity map according to one embodiment of the invention.
Figure 14B:
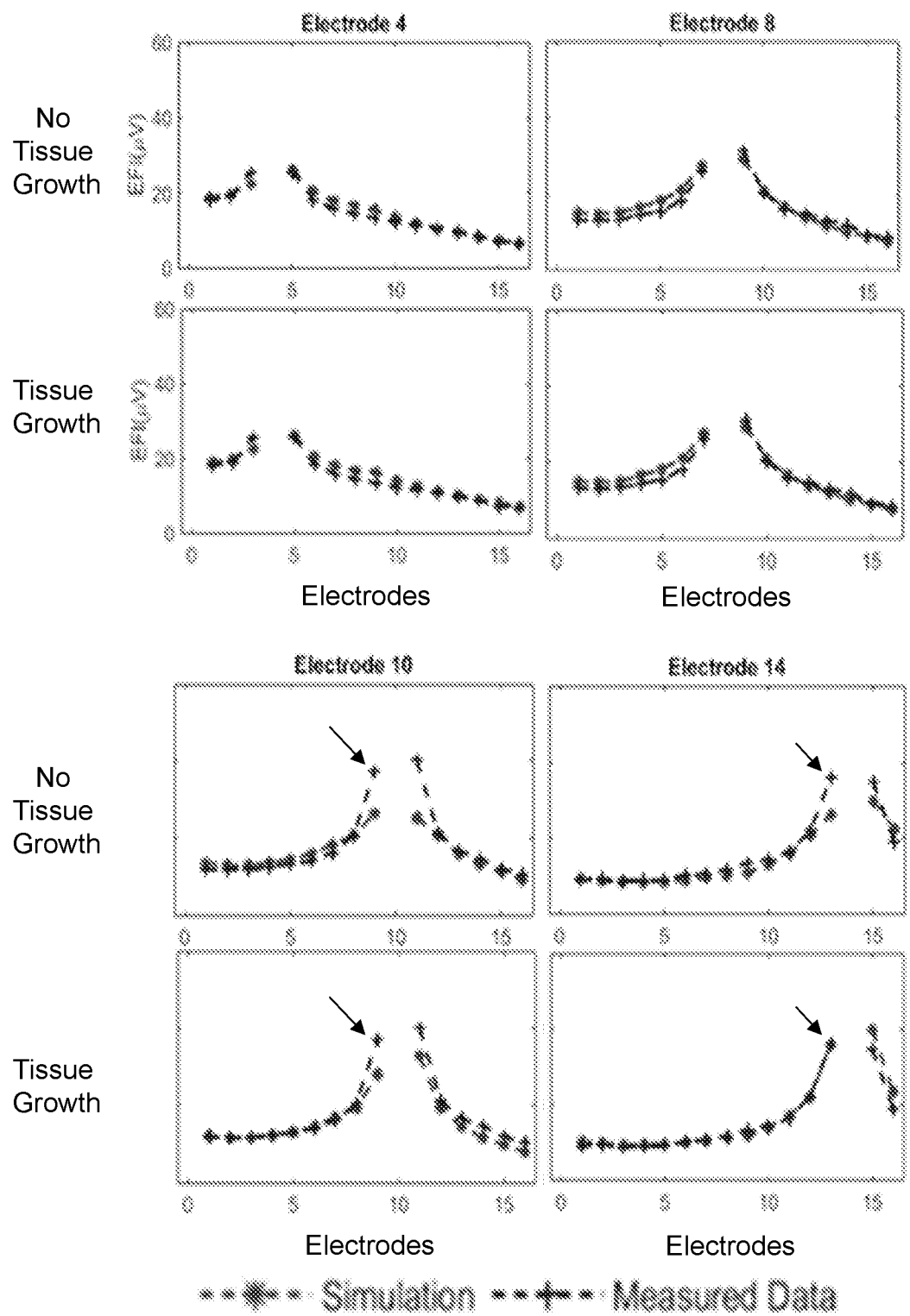
FIG. 14B shows tissue resistivity optimization using EFI according to one embodiment of the invention.

Since each patient is unique both in anatomy shape and in electrical properties, both are customized in the model using patient-specific data. First, the localizations of the electrodes and anatomical structures are used to account for patient specific anatomy shape to create a high resolution tissue resistivity map as shown in FIG. 14A, where each tissue type is assigned a different resistivity. To do this, a library of 6 high resolution $\mu$CTs of cochleae specimens with labelled tissue types is constructed. Each of the 6 tissue label maps is registered to a new patient CT with thin-plate splines, using the anatomical structure segmentations as landmarks to define the nonlinear registration. Then the label map is constructed as a majority vote of the 6 registered maps. The label map is used to construct a resistivity map that is input into a finite difference model. The model permits estimating the electric field created in the tissue when the CI electrodes are activated. Measurements of the electric field sensed by each other electrode when an electrode is activated as a current source, termed EFI, as shown in FIG. 14B, are used to customize the estimates of the resistivity of each tissue type. This is done by optimizing the resistivity values using a grid search over a range of plausible resistivity values for these tissue types so that the differences between the measured EFI and the EFI values simulated using the model are minimized. An example simulated EFI after optimization is also shown in FIG. 14B. As can be seen, excellent agreement can be achieved between simulated and measured EFI.

Nerve Fiber Activation

The inventors propose to develop models of auditory nerve fiber activation response to CI stimulation using the wHH method to model neural activation of a fiber in the form of action potentials. Specifically, a model of 75 auditory nerve fiber bundles (see FIG. 7) is provided. While each bundle could correspond to up to 500 fibers, in the prototype, a single wHH fiber model is used to represent each bundle. The wHH includes gating processes for sodium, potassium, and leakage currents. The geometry of the auditory nerve fiber modeled using NEURON is shown in FIG. 5. As shown in the figure, a nerve fiber includes several different subunits, which are peripheral nodes and internodes, somatic, pre- and post-somatic regions, and central nodes and internodes. Each of these subunits can be thought as a compartment that is modeled by an electrical circuit with distinctive electrical properties. The peripheral part of the axon contains an unmyelinated terminal, 5 nodes of Ranvier, 6 internodes and a presomatic region and has a diameter of 1 µm. The central part of the axon contains the postsomatic region, 16 internodes and 15 nodes of Ranvier and has a diameter of 2 µm. The peripheral internodes are covered with 40 shielding layers, whereas the central ones are covered with 80 layers. Finally, the soma is modeled as a perfect sphere with a diameter of 30 µm and is covered with 3 shielding layers. This model permits estimating action potentials in fibers in each nerve fiber bundle, localized as described above, and thus permits estimating which nerve fiber bundles each electrode activates in response to a given stimulus, assuming the fibers are healthy.

The preliminary models developed use a fixed set of parameters on the sodium, potassium, and leakage currents and are deterministic, not accounting for the stochastic fluctuations in the ion channels. It is thus not possible to use them to directly model the dynamic range of the number of fibers within a bundle that are recruited with a range of stimulation amplitudes. In all of the following preliminary analyses, a single fiber model is used to determine the shape of the compound action potential for the bundle, and then linearly scaled over the measured perceptual dynamic range of the contact between threshold (the lowest stimulation level perceptible) and loudest comfortable level. The models may be extended so that an accurate number of fibers are represented for each bundle and to account for stochastic fluctuations as proposed by Rattay et al. and for variations in gate parameters. Then, tuning of noise current levels and gate parameters may be performed to match electrophysiological measurements as described later.

Tissue Growth

Using the techniques described above, while excellent agreement with EFI could be achieved for most electrodes, for some subjects the measured voltage on nearby electrodes when the more basal electrodes are used as current sources is much higher than the simulation, as shown with arrows in the top EFI plots of electrodes 10 and 14 in FIG. 14B. Such local differences cannot be explained by global adjustment of tissue resistivities in the baseline tissue resistivity map, and imply that impedances of tissue locally around the electrodes is higher than expected, leading to a larger voltage gradient between the stimulating and adjacent electrodes for a fixed amount of stimulation current. This could be due to scar tissue growth around the basal portion of the electrode array. After implantation, the body can treat the electrode array as a foreign object and start forming scar/fibrous tissue around it, which is known to commonly occur with CIs from post-mortem histological studies. To account for local impedance changes due to scar tissue, the inventors propose to detect tissue growth when simulated EFI is substantially lower on adjacent electrodes than the measurement. For affected electrodes, a layer of soft-tissue is added around the electrode array in the model and optimize the thickness of this layer such that the simulation matches the measured EFI.

Figure 15:
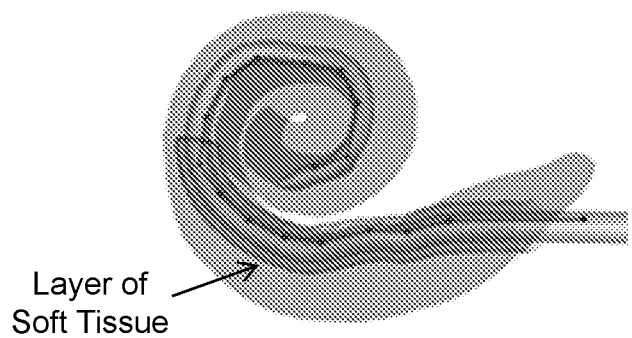
FIG. 15 shows a sagittal CT slice with the ST and the SV according to one embodiment of the invention, where a constant width thin layer of soft tissue is added.

A proof-of-concept prototype of this approach has been implemented and tested it on data from 7 subjects. With the prototype method, there is no tissue thickness optimization method applied. Instead, a constant width thin layer of soft tissue is simply added around the array with no optimization as shown in FIG. 15. Tissue growth around one or more basal contacts was estimated in 5 of 7 subjects. This procedure improved the mean percent difference between measured and simulated EFI profiles in every case. An example result is shown in the bottom EFI plots of FIG. 14B, where the arrows show where the EFI match improves after inserting tissue growth into the model. A method to detect tissue grown in vivo is novel and could have diagnostic value beyond MOCIP. There is no comprehensive ground truth to validate the accuracy of our estimates of tissue growth thickness and extent beyond post-mortem histopathologic and/or µCT analysis. Research participants will be made aware of existing temporal bone registries and asked to consider donating their temporal bones at time of death to facilitate this type of analysis in the future. In this experiment, validation may be performed in terms of accuracy in detecting the presence of tissue growth in the basal turn, where potential individuals undergoing CI revision surgery at VUMC who still have functioning devices (~25/yr) will be recruited to take part. For these individuals, the existence of tissue growth around the array in the base of the cochlea can be visualized in the operating room by the surgeon. The models are used to detect tissue growth as discussed above, and accuracy in terms of detecting the presence of tissue will be evaluated by visual confirmation. High accuracy (>90%) would confirm our interpretation of features of the EFI we hypothesize to indicate tissue growth.

Nerve Fiber Health

The inventors propose to parameterize the fiber bundle models in terms of the number of living fibers and the ratio of healthy to degenerated fibers, where the peripheral axon is degenerated but the SG soma and central axon are intact (see FIG. 5), which commonly occurs with HL. If the models accurately capture the electric field created by the electrode, the resistive properties of the tissues, and the behavior of healthy nerve fibers, in theory neural health is the only remaining factor that can account for variability in eCAPs. By tuning these parameters such that model predictions match electrophysiological measurements, it is possible to indirectly estimate the health of the neural fibers. Specifically, AGF, SOE, and RRF are collected, and tuning of the neural health parameters in the model is conducted, such that model predictions match the measured values. In particular, parameter control points are defined between each of the electrodes so that parameters for each of the 75 bundles do not need to be tuned independently. With this approach, the number of parameters to tune is proportional to the number of electrodes from which the training data is collected and overfitting can be avoided.

Figure 16:
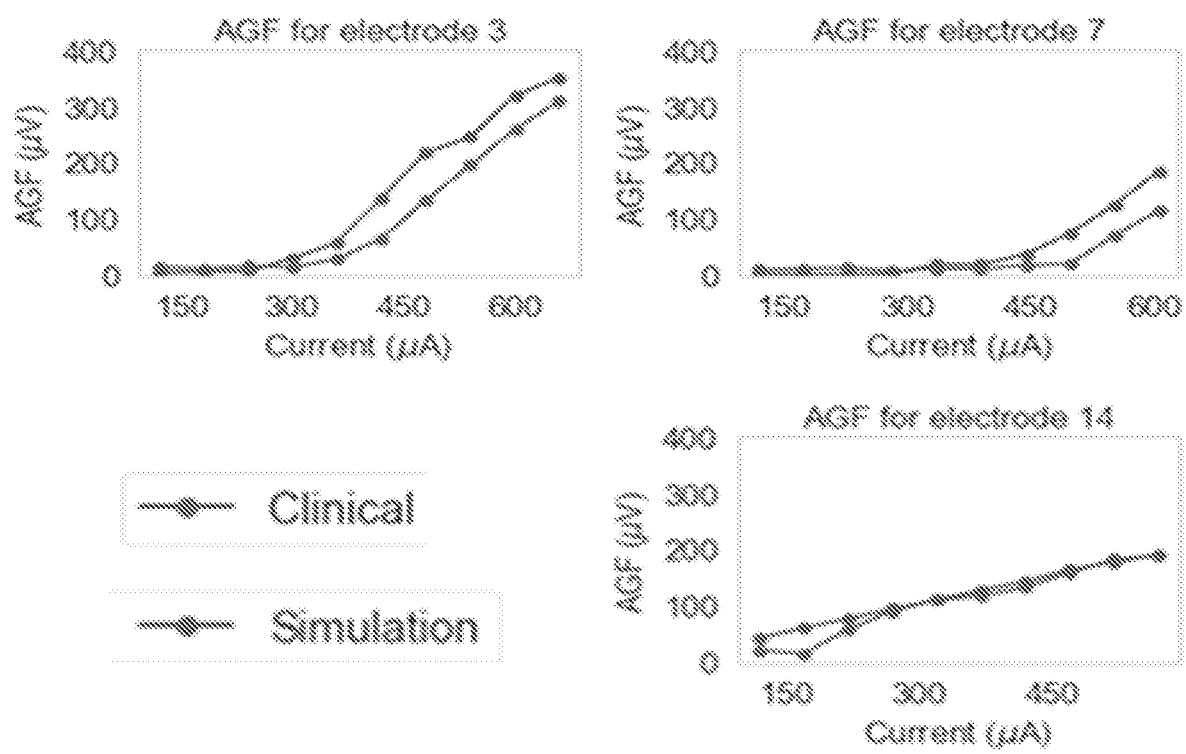
FIG. 16 shows neural health estimation using eCAP AGF according to one embodiment of the invention.

A proof-of-concept prototype of this approach has been implemented and tested it with 5 subjects. In the prototype, neural health parameters were tuned using only the AGF data, not accounted for stochastic fluctuations, and fixed gating parameters were used. An example AGF for 1 electrode simulated by the model is shown in FIG. 10. The resulting N1-P1 amplitudes can be plotted as a function of stimulating current as shown in FIG. 16, where both simulated and measured AGF are shown. As can be seen, excellent agreement between simulated and measured AGF can be obtained after tuning the neural health parameters. Mean difference across the 5 subjects between simulated and measured AGF was 135 µV before tuning and only 23 µV after tuning. However, with the additional training data and parameters for optimization, the AGF fits could be even better.

Model Validation

The best direct validation of our neural health estimates would be post-mortem histological dissection and healthy cell count. However, since these research subjects are still alive, several indirect validation methods were proposed, and each of which taken as a whole can strongly suggest the models are providing realistic estimates. First, the models can be built and trained using some eCAP measures and use them to predict others. As proof-of-concept, the prototype model was trained on AGF, and SOE for these subjects was also measured but not included in model training. The models trained with AGF are able to simulate SOE with average error of only 37 µV. Example results for four probe electrodes for one subject are shown in FIG. 17. While SOE is not entirely independent from AGF, it does capture different information about overlapping stimulation across electrodes, and good agreement between simulated and measured results suggests the physics-based models of current flow and neural activation are performing reasonably.

Second, model predictions are compared to psychophysical metrics. Specifically, the inventors propose to estimate perceptual channel overlap (PCO) by finding the threshold fraction at which the patient can no longer differentiate the sensation of current being delivered to an electrode from the sensation of a fraction of the current being simultaneously delivered to a neighboring electrode. To find the threshold, an adaptive task is used, in which the patient is asked to identify which sound is different from 3 presentations of one stimulus and 1 of the other. If the patient is successful twice in a row in identifying the sound with the different pitch, then the fraction is decreased. If the patient is unsuccessful, the fraction is increased making the task easier. The task is repeated with the goal of finding the fraction for which the patient has a 0.707 success probability. The test can be conducted 3 times for each electrode pair to find the final threshold as the mean value across all 3 trials. Lower thresholds correspond to less PCO. Then the inventors propose to measure model-estimated channel overlap (MCO) by counting the fraction of fibers one electrode stimulates that another electrode also stimulates. If the model is accurate, there should be a high correlation between PCO and MCO across different electrode sites. As proof-of-concept, MCO and PCO were recorded for four patients. PCO required approximately 20 minutes of testing for each electrode pair, so due to time constraints a total of 15 electrode pairs, rather than all electrode pairs, across the 4 patients were tested. We found a moderately strong correlation coefficient (CC) of 0.69 between MCO and PCO for these 4 patients. For comparison, the CC between modiolar distance of the same electrode pairs and PCO was also computed, which was found to be 0.39. These results indicate that MCO is a better estimate for channel interaction than modiolar distance. Thus, deactivation to reduce channel interaction based on MOCIP should lead to even better CI performance than IGCIP.

Figure 18:
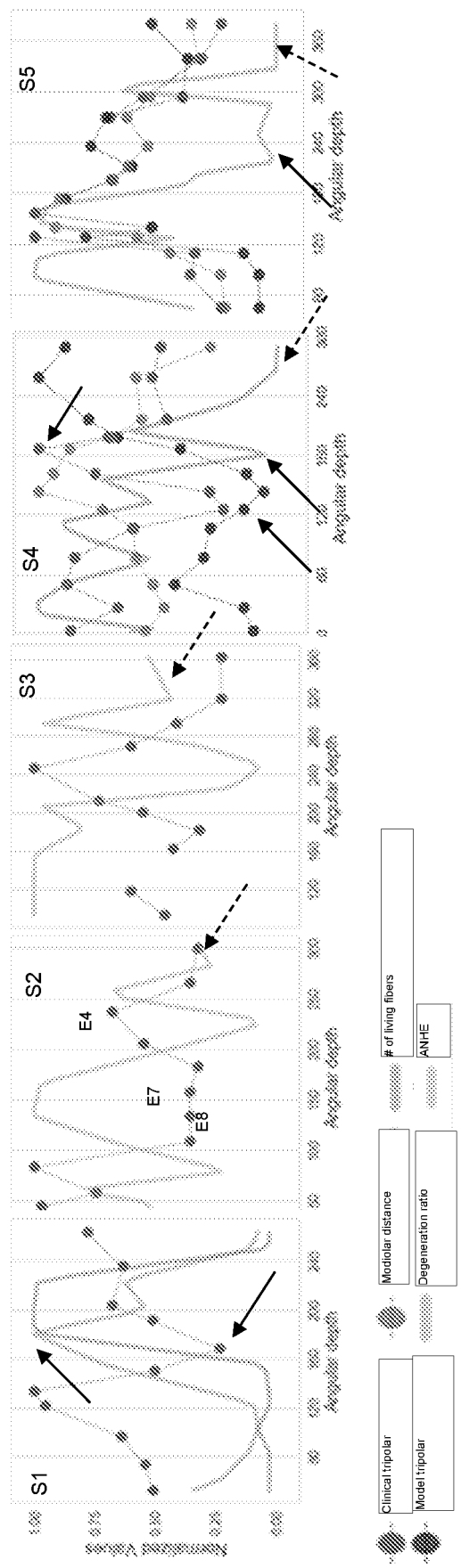
FIG. 18 shows tripolar thresholds and model estimates for 5 subjects according to one embodiment of the invention.

Another psychophysical metric, tripolar stimulation thresholds, has been introduced as a correlate of neural health. Tripolar stimulation focuses the region of stimulation to a smaller group of nerves by sinking current to the electrodes neighboring the source electrode, as opposed to a distant ground as is done with monopolar stimulation. Thus, tripolar threshold levels are more sensitive to the health of the local nerves. Their use to measure neural health has not become widespread because they are also sensitive to the distance to neural sites and tissue resistance, making it difficult to estimate neural health with tripolar thresholds alone. However, with the context provided by the model, it is possible to understand features that correlate with distance to the nerve sites versus neural health. Higher thresholds should correspond to areas with poorer neural health and/or greater distance to the nerves. As proof-of-concept, tripolar thresholds on 5 subjects have been measured, as shown in FIG. 18. In each plot as shown in FIG. 18, the x-axis shows angular depth into the cochlea. There is a consistent shift in the visual correlation of the neural health estimates and the tripolar thresholds corresponding to a 1.2 mm shift along RC. This artifact has been corrected prior to the following analyses and will be discussed further in the following section. For S1, clinical tripolar thresholds, estimated degeneration ratio and estimated number of healthy fibers are all shown. Excellent negative correlation can be seen between the features of the tripolar thresholds and the neural health estimates. The single peak with full healthy fibers corresponds to the smallest threshold (dark arrows), and larger thresholds are seen where health is estimated to be lower. For S2 and S3, the myelination and number of fiber terms were correlated with CC>0.5. Thus, the two are combined into the auditory nerve health estimate (ANHE) which equals (number of healthy fibers)*(0.5+0.5*(myelination ratio)). ANHE is larger when more healthy fibers are estimated to be present. An example ANHE result is shown in FIG. 7, where regions of fiber bundles that are estimated to be healthy and ones that are not are clearly differentiated. For S2 and S3, again excellent agreement between ANHE and tripolar thresholds can be seen overall. For S4, a sharp dip in threshold can be seen around 140 degrees that does not correspond to an increase in estimated neural health nor a drop in modiolar distance. For this subject, the array translocated through the basilar membrane from ST to SV at this location. While the electrodes are more distant to the modiolus, they are very close to the peripheral part of the fibers where they reach the basilar membrane (see FIG. 13). When tripolar stimulation is performed with the model and stimulation levels is optimized to find thresholds in the model, a similar dip appears in model-predicted thresholds at 140 degrees (dark arrow). A threshold spike at 180 degrees well correlates with an estimated neural health drop (light arrows). For S5, tripolar thresholds were unobtainable in the middle of the array (E6-E11) because they were so high they were unobtainable within the stimulation level limits on the CI software. This well correlates with the region for which the degeneration ratio is estimated to be poor (black arrow).

While AGFs and other functions of eCAPs contain information about neural activation and the ENI critical for constructing our models, these promising sources of information have been used surprisingly rarely, for programming despite being widely available for decades, because they have been difficult to interpret. However, results with these 5 subjects demonstrate how the models provide a physical explanation for the eCAP measurements, and can offer clinicians an unprecedented direct estimation of the ENI.

Improved Nerve Fiber Segmentation

While good agreement between model predictions and tripolar thresholds can be seen overall, the worst agreement is seen at the deeper insertion depths near 300 degrees, where neural health is consistently estimated to be low (dotted arrows in FIG. 18). This is likely because the models constructed do not include fibers that exist from 540 degrees to 900 degrees (dashed fibers in FIG. 13) because RC, which is used as a landmark to identify the fiber locations, is difficult to visualize in µCT beyond 540 degrees. Since fibers in the apical turns of the cochlea are very close together, electrodes located near 300 degrees and beyond could also stimulate fibers corresponding to deeper turns. This is especially true when the electrode array is translocated from ST to SV as it is for patients 4 and 5, since at this depth the SV is closer to the SG cells of the next turn as can be appreciated in FIG. 13, where the SV at 270 degrees is closer to the SG of the 630 degree nerve fibers. Further, the fibers take an oblique angle from RC into the OSL as can be seen by histology, but were modeled as taking a direct radial path since their true shape cannot be well visualized in µCT. This could also explain the 1.2 mm shift in neural health estimates relative to measured tripolar thresholds. The inventors propose to improve the fiber segmentation approach using an improved training dataset by complementing μCT with histological dissection on 20 fresh cadaveric cochleae specimens. Registering the histological slices to the μCT will permit visualization of the fiber shape as well as the entirety of the RC. This dataset will permit improving and extending our fiber segmentation method as well as validating it with a comprehensive ground truth.

Performance Evaluation

The inventors propose to test MOCIP-based strategies that aim to alleviate channel interaction artifacts, since IGCIP strategies that aimed to reduce channel interaction were the most successful in prior studies. Performance of new maps will be assessed quantitatively using the minimum speech test battery (MSTB). The MSTB outlines the administration of Consonant Nucleus Consonant (CNC) monosyllabic words and "AzBio" sentences in quiet and noise. Estimates of spectral resolution will be obtained using spectral modulation detection (SMD), which is a non-speech based hearing performance metric that provides a psychoacoustic estimate of spectral resolution, i.e., the ability of the auditory system to decompose a complex spectral stimulus into its individual frequency components. Qualitative performance will be measured using the Abbreviated Profile of Hearing Aid Benefit (APHAB).

MOCIP-Neural Health

The inventors propose reduced activation in regions with poor neural health using electrode deactivation or custom focused channels. As proof-of-concept, the everyday use map for S2 in FIG. 18 was modified and tested acutely. Map "M4" was created in which an electrode in a region corresponding to estimated poor neural health (E4) was deactivated, respectively. Note that map changes, especially ones that require frequency remapping as does deactivation, are biased negatively in the acute condition due to lack of experience, and thus we created a control map M8 (deactivating electrode E8, which sits in high health region) and hypothesized M4 would perform better than M8. After listening to each new map with a 2 minute pre-recorded passage, performance was assessed. The results are shown in Table 2. It was found that CNC words were 6% better, AzBio sentences in quiet 12% better, and AzBio+10 dB signal-to-noise ratio 8% better with map M4 compared to M8. The subject also qualitatively scored M4 as having greater listening ease. M4 scored better in quiet compared to the everyday program, which is remarkable given the acute testing condition.

TABLE 2

Preliminary MOCIP results with S2.
Table 1 Preliminary MOCIP results with S2

| Map | Wrd. (%) | Sent. Qt. (%) | Sent + 1 OdB (%) | SMD (%) | Listening ease (1-10) |
| --- | --- | --- | --- | --- | --- |
| Everyday | 66 | 83 | 57 | 67 | 5 |
| M4 | 74 | 87 | 33 | | 3 |
| M8 | 68 | 75 | 25 | | 1 |
| Reorder | 80 | 97 | 49 | 77 | 7 |
| pTP | 82 | 95 | 64 | 77 | 7 |

MOCIP-Channel Sequence

The inventors propose to develop a method to determine patient-customized sequence in which the channels are ordered. Channel interaction artifacts could be reduced if the sequence was modified such that the amount of time between firing two channels that mask each other is maximized within the stimulation sequence. The model is used to determine the amount of time before activating a channel that is required for the nerves it stimulates to activate similarly to steady state conditions when following stimulation by any other channel. An example of these data for S2 is shown in FIG. 19, where S2's everyday map is comprised of a total of 10 channels. For every probe channel on the x-axis, shown is the amount of time in milliseconds required to wait after stimulation by any masker channel on the y-axis such that stimulation by the probe results in action potentials that are 95% in agreement with those that would be generated by stimulating the probe from steady state. As shown in FIG. 19, all electrodes require some time for masking release from adjacent neighbor electrodes. Channels 1-5 and 10 are generally not very sensitive to prior stimulation of adjacent channels (black oval). Channels 6-9 are the most sensitive channels to prior stimulation from adjacent channels (red oval). Thus, the stimulation order for these channels is customized such that channels 6-9 are spaced at larger intervals by shortening the intervals for 1-5. Such an approach could potentially be more successful than deactivation-based strategies, since it alleviates channel interaction without the need to reduce the number of channels. Customizing the models using the RRF data will be critical for accurate modeling of masking times as RRF contains neural timing information.

Although the prototype models use default neural timing behavior, as proof-of-concept, this strategy has been implemented for S2. The firing order in the everyday map was by default [1,5,9,2,6,10,3,7,4,8], placing channels 7 & 8 within one interval in the sequence. After changing the order to [1,5,8,2,4,7,3,10,6,9], channels 6-9 have at least two intervals between neighbors. After acute testing as described above, the results labeled "Reorder" in Table 2 were obtained. The subject immediately performed substantially better in terms of speech recognition in quiet and reported greater ease of listening and clarity compared to the everyday map. SMD increased relative to the everyday map, indicating that a reduction in channel interaction was achieved.

MOCIP-Current Focusing

Current focusing is another approach that has great promise for reducing channel interaction. Focusing is generally implemented using a tripolar electrode configuration. However, no widespread strategies have come into use, with perceptual response and hearing outcomes with multipolar stimulation being highly variable, and with power demands that significantly shorten battery life. The effectiveness of current focusing could be improved by custom-shaped focused channels that account for the ENI so that each active channel stimulates healthy populations of nerves that are as independent as possible. Further, to alleviate the effect of power demands, the inventors propose to select specific channels for which focusing would be most beneficial. The best candidates for focusing are channels that experience high stimulation overlap using monopolar stimulation, but lie near healthy nerves that are able to be selectively recruited by focused stimulation. A proof-of-concept test has been performed with S2. FIG. 20 shows the matrix of fraction of overlapping fibers stimulated by each pair of channels. With greatest overlap fractions (>0.5) for channels 6-8, and with E7 lying in a region estimated to be healthy (see FIG. 18), channels 6 and 7 were chosen to convert to partial tripolar (pTP) channels, where 50% of the stimulation current returns to flanking contacts while 50% still returns to the distant ground. Acute testing after making this map change showed excellent improvement in speech recognition in quiet and noise as well as subjective benefit over the everyday map (see Table 2).

The everyday map for S2 is an IGCIP program with >2 years use. Thus, the preliminary results with MOCIP presented above demonstrate the promise of MOCIP for improving upon IGCIP (which performed 12%, 18%, and 10% better than standard-of-care on CNC words, AzBio quiet, and AzBio+5 dB noise) by using the critical information about the ENI provided by the comprehensive patient-specific models. Long-term use of the experimental maps would likely lead to even better results.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

REFERENCES

[1] American Speech-Language Hearing Association (2008). Incidence and prevalence of hearing loss and hearing aid use in the United States—2008 edition.

[2] Buss E, Pillsbury H C, Buchman C A, Pillsbury C H, Clark M S, Haynes D S, Labadie R F, Amberg S, Roland P S, Kruger P, Novak M A, Wirth J A, Black J M, Peters R, Lake J, Wackym P A, Firszt J B, Wilson B S, Lawson D T, Schatzer R, S. DHP, Barco A L: Multicenter U.S. Bilateral med-el cochlear implantation study: Speech perception over the first year of use. Ear Hear 2008; 29:20-32.

[3] Dorman M F, Yost W, Wilson B S, Gifford R H: Speech perception and sound localization by adults with bilateral cochlear implants. Seminars in Hearing 2009; 32:73-89.

[4] Gifford R H, Shallop J K, Peterson A M. (2008). Speech Recognition Materials and Ceiling Effects: Considerations for Cochlear Implant Programs. Audiol Neurotol, 13:193-205.

[5] Dorman M F, Sheffield S W, Teece K, Olund A P, Gifford R H. (in press). Availability of binaural cues for bilateral cochlear implant recipients and bimodal listeners with and without hearing preservation. Audiol Neurotol.

[6] Litovsky R Y, Parkinson A, Arcaroli J, Sammeth C: Simultaneous bilateral cochlear implantation in adults: A multicenter clinical study. Ear Hear 2006; 27:714-730.

[7] Michelle Hughes. Objective measures in cochlear implants, $1^{st}$ edition. Plural publishing, 2012.

[8] Rubenstein J. T., "How cochlear implants encode speech," Curr Opin Otolaryngol Head Neck Surg. 12(5): 444-8, 2004.

[9] Srijata Chakravorti and Jack H. Noble (co-first authors), Rene H. Gifford, Benoit M. Dawant, Brendan O'Connell, Jianing Wang, Robert F. Labadie, "Further evidence of the relationship between cochlear implant electrode positioning and hearing outcomes," Otology & Neurotology, June 2019—Volume 40—Issue 5—p 617-624

[10] Holden L K, Finley C C, Firszt J B, Holden T A, Brenner C, Potts L G, Gotter B D, Vanderhoof S S, Mispagel K, Heydebrand G, Skinner M W., "Factors affecting open-set word recognition in adults with cochlear implants," Ear Hear. 34(3):342-60, 2013.

[11] Jack Noble and Robert Labadie, "Preliminary results with image-guided cochlear implant insertion techniques," Otology & Neurotology, vol. 39(7), pp. 922-928, 2018.

[12] Wilson B. S., Finley C. C., Lawson, D. T., Wolford, R. D., Eddington, D. K., Rabinowitz, W. M., "Better speech recognition with cochlear implants," Nature 352, 236-238, 1991.

[13] Bierer J A (2007). Threshold and channel interaction in cochlear implant users: evaluation of the tripolar electrode configuration. J Acoust Soc Am, 121(3): 1642-53.

[14] Bierer J A (2010). Probing the electrode-neuron interface with focused cochlear implant stimulation. Trends Amplif, 14(2): 84-95.

[15] Noble J H, Labadie R F, Majdani O, Dawant B M., Automatic segmentation of intra-cochlear anatomy in conventional CT. IEEE Trans. on Biomedical. Eng. 58(9), 2011.: 2625-32. PMID 21708495

[16] Noble, J. H., Gifford, R. H., Labadie, R. F., Dawant, B. M., "Statistical Shape Model Segmentation and Frequency Mapping of Cochlear Implant Stimulation Targets in CT," N. Ayache et al. (Eds.): MICCAI 2012, Part II, LNCS 7511, pp. 421-428. 2012. PMID 23286076

[17] Noble J H, Labadie R F, Gifford R H, Dawant B M, "Image-guidance enables new methods for customizing cochlear implant stimulation strategies," IEEE Trans. on Neural Systems and Rehabilitiation Engineering, vol. 21(5):820-9, 2013. PMID 23529109

[18] Noble J H, Gifford R H, Hedley-Williams A J, Dawant B M, and, Labadie R F, "Clinical evaluation of an image-guided cochlear implant programming strategy," Audiology & Neurotology, vol. 19, pp. 400-11, 2014. PMC4305276

[19] Noble J. H., Hedley-Williams A. J., Sunderhaus L. W., Dawant B. M., Labadie R. F., Camarata S. M., Gifford R. H., "Initial results with image-guided cochlear implant programming in children," Otology & Neurotology 37(2), pp. 69-9, 2016. PMC4849538

[20] Fu, Q. J., Shannon, R. V., & Galvin, J. J. 3rd. (2002). Perceptual learning following changes in the frequency-to-electrode assignment with the Nucleus-22 cochlear implant. Journal of the Acoustical Society of America, 112(4), 1664-1674

[21] Nadol, J. B., Young, Y.-S., & Glynn, R. J. (1989). Survival of Spiral Ganglion Cells in Profound Sensorineural Hearing Loss: Implications for Cochlear Implantation. Annals of Otology, Rhinology & Laryngology, 98(6), 411-416.

[22] Mishaela DiNino, Gabrielle O'Brien, Steven M. Bierer, Kelly N. Jahn, Julie G. Arenberg, "The Estimated Electrode-Neuron Interface in Cochlear Implant Listeners Is Different for Early-Implanted Children and Late-Implanted Adults," Journal of the Association for Research in Otolaryngology, June 2019, Volume 20, Issue 3, pp 291-303

[23] Mendel L L, Mustain W D, Magro J, "Normative Data for the Maryland CNC Test," Journ. Of Am. Acad. Audiol., vol. 25, pp. 775-781, 2014.

[24] Kochkin S, "The efficacy of hearing aids in achieving compensation equity in the workplace," The Hearing Journal, vol. 63 (10), pp. 19-28, 2010.

[25] Labadie R F, Noble J H, Hedley-Williams A J, Sunderhaus L W, Dawant B M, Gifford R H. "Results of Postoperative, CT-based, Electrode Deactivation on Hearing in Prelingually Deafened Adult Cochlear Implant Recipients. Otology & Neurotology 2016 February; 37(2):137-45. PMC4712086.

[26] Theodore R. McRackan, Jack H. Noble, Eric P. Wilkinson, Dawna Mills, Mary S. Dietrich, Benoit M. Dawant, Rene H. Gifford, Robert F. Labadie, "Implementation of Image-Guided Cochlear Implant Programming at a Distant Site," Otolaryngology—Head & Neck Surgery, vol. 156(5), pp. 933-937, 2017. PMID: 28374640.

[27] Zhao Y, Dawant B M, Labadie R F, Noble J H. "Automatic localization of cochlear implant electrodes in CT. Med Image Comput Comput Assist Interv. 2014; 17(Pt 1):331-8. PMC4426961.

[28] Noble, J. H. and Dawant, B. M., "Automatic graph-based localization of cochlear implant electrodes in CT," Lecture Notes in Computer Science—Proceedings of MICCAI, vol. 9350, pp. 152-9, 2015. PMC4854292

[29] Zhao Y, Dawant B M, Noble J H. Automatic selection of the active electrode set for image-guided cochlear implant programming. Journal of medical imaging 2016 July; 3(3):035001 PMC5031788.

[30] Zhang D, Liu Y, Noble J H, Dawant B M. Localizing landmark sets in head CTs using random forests and a heuristic search algorithm for registration initialization. Journal of medical imaging. 2017 October; 4(4):044007. PMC5722233.

[31] Zhang D, Zhao Y, Noble J H, Dawant B M. Selecting electrode configurations for image-guided cochlear implant programming using template matching. Journal of medical imaging. 2018 April; 5(2):021202. PMC5724566.

[32] Y Zhao, S Chakravorti, R F Labadie, B M Dawant, J H Noble, "Automatic graph-based method for localization of cochlear implant electrode arrays in clinical CT with sub-voxel accuracy," Medical image analysis, vol. 52, pp. 1-12, 2019.

[33] Yiyuan Zhao, Robert Labadie, Benoit Dawant, Jack Noble, "Validation of cochlear implant electrode localization techniques using μCTs," J. of Medical Imaging, 5(3), 035001 (2018).

[34] Yiyuan Zhao, Benoit Dawant, and Jack Noble., "Automatic localization of closely-spaced cochlear implant electrode arrays in clinical CTs," Med. Phys., vol 45 (11), pp. 5030-5040, 2018.

[35] Chakravorti S, Bussey B J, Zhao Y, Dawant B M, Labadie R F, Noble J H. Cochlear implant phantom for evaluating computed tomography acquisition parameters. Journal of medical imaging. 2017 October; 4(4):045002. PMC5689133.

[36] Cakir A, Labadie R F, Zuniga M G, Dawant B M, Noble J H. Evaluation of Rigid Cochlear Models for Measuring Cochlear Implant Electrode Position. Otology and Neurotology. 2016 December; 37(10):1560-1564. PMC5240585.

[37] Connell B P, Cakir A, Hunter J B, Francis D O, Noble J H, Labadie R F, Zuniga G, Dawant B M, Rivas A, Wanna G B. Electrode Location and Angular Insertion Depth Are Predictors of Audiologic Outcomes in Cochlear Implantation. Otology & neurotology, 2016 September; 37(8):1016-23. PMC4983244.

[38] Connell B P, Hunter J B, Gifford R H, Rivas A, Haynes D S, Noble J H, Wanna G B. Electrode Location and Audiologic Performance After Cochlear Implantation: A Comparative Study Between Nucleus CI422 and CI512 Electrode Arrays. Otology and Neurotology. 2016 September; 37(8):1032-5. PMC4988342.

[39] Zuniga M G, Rivas A, Hedley-Williams A, Gifford R H, Dwyer R, Dawant B M, Sunderhaus L W, Hovis K L, Wanna G B, Noble J H, Labadie R F. Tip Fold-over in Cochlear Implantation: Case Series. Otology and Neurotology. 2017 February; 38(2):199-206. PubMed PMID: 27918363.

[40] Rivas A, Cakir A, Hunter J B, Labadie R F, Zuniga M G, Wanna G B, Dawant B M, Noble J H. Automatic Cochlear Duct Length Estimation for Selection of Cochlear Implant Electrode Arrays. Otology and Neurotology. 2017 March; 38(3):339-346. PMC5335919.

[41] Wang J, Dawant B M, Labadie R F, Noble J H. Retrospective Evaluation of a Technique for Patient-Customized Placement of Precurved Cochlear Implant Electrode Arrays. Otolaryngology—head and neck surgery. 2017 March 1; 194599817697298. PMID: 28374623.

[42] Connell B P, Hunter J B, Haynes D S, Holder J T, Dedmon M M, Noble J H, Dawant B M, Wanna G B. Insertion depth impacts speech perception and hearing preservation for lateral wall electrodes. The Laryngoscope. 2017 Mar. 17.

[43] BP O'Connell, M T Dillon, J H Noble, G B Wanna, E R King, H C Pillsbury, K B Brown, "Insertion depth impacts speech perception and hearing preservation outcomes for lateral wall electrodes," Journal of Hearing Science, Vol. 8(2), 2018.

[44]. Kanthaiah Koka, William Jason Riggs, Robert Dwyer, Jourdan Taylor Holder, Jack H Noble, Benoit M Dawant, Amanda Ortmann, Carla V Valenzuela, Jameson K Mattingly, Michael M Harris, Brendan P O'Connell, Leonid M Litvak, Oliver F Adunka, Craig Alan Buchman, Robert F Labadie, "Intra-Cochlear Electrocochleography During Cochear Implant Electrode Insertion Is Predictive of Final Scalar Location," Otology & Neurotology vol. 39(8) pp. e654-e659, 2018.

[45] Rene H Gifford, Jack H Noble, Stephen M Camarata, Linsey W Sunderhaus, Robert T Dwyer, Benoit M Dawant, Mary S Dietrich, Robert F Labadie, "The relationship between spectral modulation detection and speech recognition: Adult versus pediatric cochlear implant recipients," Trends in Hearing, vol. 22, 2018.

[46] Holder J T, Kessler D M, Noble J H, Gifford R H, Labadie R F, "Prevalence of Extracochlear Electrodes: Computerized Tomography Scans, Cochlear Implant Maps, and Operative Reports," Otology & Neurotology, vol. 39(5), e325-e331, 2018.

[47] Davis T J, Zhang D, Gifford R H, Dawant B M, Labadie R F, Noble J H. Relationship Between Electrode-to-Modiolus Distance and Current Levels for Adults With Cochlear Implants. Otol Neurotol. 2016 January; 37(1): 31-37. PMCID: PMC4675044.

[48] Ahmet Cakir, Robert T Dwyer, Jack H Noble, "Evaluation of a high-resolution patient-specific model of the electrically stimulated cochlea," Journal of Medical Imaging, vol. 4(2), 025003, 2017.

[49] T. F. Cootes, C. J. Taylor, C. H. Cooper, and J. Graham, Active shape models-their training and application. Computer Vision and Image Understanding, Vol. 61, 1995. pp. 38-59.

[50] The Length of the Organ of Corti in Man, Hardy M, American Journal of Anatomy, 62(2), 1938, p. 179-311.

[51] Pelosi S and Noble J (co-first authors), Dawant B, and Labadie R F. "Analysis of inter-subject variations in promontory and intracochlear anatomy for cochlear implantation," Otology and Neurotology vol. 34(9), pp. 1675-1680, 2013.

[52] Wanna, G. B., Noble J. H., Carlson, M. L., Gifford, R. H., Dietrich, M. S., Haynes, D. S. Dawant, B. M., and Labadie, R. F., "Impact of Electrode Design and Surgical Approach on Scalar Location and Cochlear Implant Outcomes," Laryngoscope, vol. 124(S6), pp. S1-7, 2014.

[53] Wanna G B, Noble J H, Gifford R H, Dietrich M S, Sweeney A D, Zhang D, Dawant B M, Rivas A, Labadie R F. "Impact of Intrascalar Electrode Location, Electrode Type, and Angular Insertion Depth on Residual Hearing in Cochlear Implant Patients: Preliminary Results." Otol Neurotol. 36(8):1343-8, 2015.

[54] F. L. Bookstein, "Principal warps: Thin-plate splines and the decomposition of deformations," IEEE Transactions on Pattern Analysis and Matching Intelligence, vol. 11(6), 1989, pp. 567-585.

[55] Whiten D, "Electro-anatomical models of the cochlear implant," Ph.D. Thesis, Massachusetts Institute of Technology Library, 2007.

[56] Rattay F, Lutter P, Felix H., "A model of the electrically excited human cochlear neuron. I. Contribution of neural substructures to the generation and propagation of spikes," Hearing Research; 153; 43-63, 2001.

[57] Rattay, F., "Basics of hearing theory and noise in cochlear implants," Chaos Solitons Fractals 11: 1875-84, 2000.

[58] Li P M, Somdas M A, Eddington D K, Nadol J B Jr. Analysis of intracochlear new bone and fibrous tissue formation in human subjects with cochlear implants. Ann Otol Rhinol Laryngol. 2007 October; 116(10):731-8. PMID: 17987778

[59] Zwolan T. A., Collins L. M., Wakefiled G. H., "Electrode discrimination and speech recognition in postlingually deafened adult cochlear implant subjects," J. Acoust. Soc. Am. 102(6): 3673-85, 1997.

[60] Long, C. J., Holden, T. A., McClelland, G. H., Parkinson, W. S., Shelton, C., Kelsall, D. C., . . . Smith, Z. M. (2014). Examining the electro-neural interface of cochlear implant users using psychophysics, CT scans, and speech understanding. Journal of the Association for Research in Otolaryngology: JARO, 15(2), 293-304. (PMID: 24477546).

[61] Peterson G E, Lehiste I. (1962). Revised CNC lists for auditory tests. J Speech Hear Disord. 27:62-70.

[62] Spahr A. J., Dorman M. F., Litvak L. M., Van Wie S., Gifford R. H., Loizou P. C., Loiselle L. M., Oakes T., Cook S., "Development and validation of the AzBio sentence lists," Ear Hear. 33(1): 112-7, 2012.

[63] Saoji A A, Litvak L, Spahr A J, Eddins D A. (2009). Spectral modulation detection and vowel and consonant identifications in cochlear implant listeners. J Acoust Soc Am. 126(3):955-8.

[64] Henry B. A., Turner C. W., "The resolution of complex spectral patterns by cochlear implant and normal-hearing listeners," J Acoust Soc Am 113(5):2861-73, 2003.

[65] Drennan W R, Won J H, Nie K, Jameyson E, Rubinstein J T. (2010). Sensitivity of psychophysical measures to signal processor modifications in cochlear implant users. Hear Res. 262(1-2): 1-8.

[66] Gifford R H, Hedley-Williams, A, Spahr, AJ. Clinical assessment of spectral modulation detection for cochlear implant recipients: a non-language based measure of performance outcomes. Int J Audiol. 2014 March; 53(3): 159-64.

[67] Cox R M, Alexander G C. (1995). The abbreviated profile of hearing aid benefit. Ear Hear. 16(2): 176-86.

[68] Berenstein C K, Mens L H, Mulder J J, Vanpoucke F J. (2008). Current steering and current focusing in cochlear implants: comparison of monopolar, tripolar and virtual channel electrode configurations. Ear Hear. 29(2):250-60.

[69] Landsberger D M, Padilla M, Srinivasan A G. (2012). Reducing current spread using current focusing in cochlear implant users. Hear Res. 284(1-2):16-24.

[70] Srinivasan A G, Padilla M, Shannon R V, Landsberger D M. (2013). Improving speech perception in noise with current focusing in cochlear implant users. Hear Res. 299:29-36.

[71] Baer and Moore, 1994 T. Baer and B. C. J. Moore, Effects of spectral smearing on the intelligibility of sentences in the presence of interfering speech. J. Acoust. Soc. Am., 95 (1994), pp. 2277-2280.

[72] Stakhovskaya O, Spridhar D, Bonham B H, Leake P A. Frequency Map for the Human Cochlear Spiral Ganglion: Implications for Cochlear Implants. Journ. Assoc. Res. Otol. 8, 2007.: 220-233.

[73] MSTB: The new minimum speech test battery. http://auditorypotential.com/MSTB.html, 2011

[74] Tyler R. S., Preece J. P., Lansing C. R., Otto S. R., Gantz B. J., "Previous experience as a confounding factor in comparing cochlear-implant processing schemes," J. Speech Hear. Res. 29: 282-7, 1986.

[75] Carnevale, N. T. and Hines, M. L. The NEURON Book. Cambridge, UK: Cambridge University Press, 2006.

What is claimed is:

1. A method for performing model-based cochlear implant programming (MOCIP) on a living subject with a cochlear implant (CI) to determine stimulation settings of a patient-customized electro-neural interface (ENI) model, comprising:

localizing an electrode array of the CI and intracochlear structures of the living subject to determine patient-specific electrode positions of the CI and a patient-specific anatomy shape;

generating a CI electric field model based on the patient-specific electrodes positions of the CI and the patient-specific anatomy shape; and establishing an auditory nerve fiber (ANF) bundle model using the CI electric field model, and estimating neural health of the living subject using the ANF bundle model, wherein the estimating the neural health of the living subject comprises:

establishing the ANF bundle model with a plurality of ANF bundles, wherein each of the ANF bundles includes a plurality of fibers;

simulating electrically evoked compound action potentials (eCAPs) in each of the fibers of the ANF bundles, wherein the eCAPs are measured by amplitude growth functions (AGFs), spread of excitation (SOE) functions, and refractory recovery functions (RRFs); and estimating, for the electrodes of the CI, the ANF bundles activated by each of the electrodes in response to a given stimulus; and performing validation of the ANF bundle model by:

training the ANF bundle model using the eCAPs measured by one of the AGFs, SOE functions and RRFs; and estimating the neural health of the living subject using the trained ANF bundle model by simulating the eCAPs measured by a different one of the AGFs, SOE functions and RRFs.

2. The method of claim 1, wherein the patient-specific anatomy shape is determined by:
  obtaining a plurality of micro computed tomography (μCT) images of a plurality of cochleae specimens;
  creating a non-rigid statistical shape model using the μCT images;
  fitting the non-rigid statistical shape model to an external boundary of the cochlea of the living subject in a computed tomography (CT) image of a cochlea of the living subject to localize positions of scala tympani (ST), scala vestibuli (SV) and modiolus of the living subject; and
  determining estimated positions of ANF bundles of the living subject.

3. The method of claim 2, wherein the μCT images include μCT images of at least 8 cochleae specimens.

4. The method of claim 2, wherein the estimated positions of the ANF bundles are determined by:
  delineating Rosenthal's Canal (RC) and internal auditory canal (IAC) in the μCT images;
  registering, with localized surfaces of the ST, the SV and the modiolus, estimations of fiber endpoints of the RC and the IAC delineated in the μCT images to the CT image using thin-plate splines; and
  tracing estimated fiber bundle paths of the ANF bundles from the fiber endpoints between the ST and the SV through the RC and out to the IAC.

5. The method of claim 2, wherein the patient-specific electrode positions of the CI are determined by identifying, from the μCT images, center lines of bright tubes or blobs representing the electrode array.

6. The method of claim 1, wherein the generating the CI electric field model comprises:
  generating a tissue resistivity map for the living subject based on the patient-specific electrodes positions of the CI and the patient-specific anatomy shape;
  inputting the tissue resistivity map to a finite difference model to simulate electric fields created in tissues of the living subject when electrodes of the CI are activated;
  performing electric field imaging (EFI) to measure the actual electric fields sensed by other electrodes of the CI when one of the electrodes of the CI is activated as a current source; and
  optimizing resistivity values of the tissues in the tissue resistivity map based on the electric field simulated by the finite difference model and the actual electric fields measured by EFI.

7. The method of claim 6, wherein the optimizing the resistivity values of the tissues comprises:
  comparing, for each of the electrodes of the CI, the electric fields simulated by the finite difference model and the actual electric fields measured by EFI; and
  in response to determining, for a specific electrode of the electrodes, the electric field simulated by the finite difference model corresponding to the specific electrode is significantly lower than the actual electric fields measured by EFI corresponding to the specific electrode, determining tissue growth occurs at the specific electrode, and adding a soft tissue layer around the specific electrode in the finite difference model.

8. The method of claim 1, wherein each of the fibers in the ANF bundle model is a warmed Hodgkin-Huxley (wHH) fiber.

9. The method of claim 1, wherein the estimating the neural health of the living subject further comprises:
  measuring actual eCAPs for the electrodes of the CI; and
  tuning neural health parameters of the ANF bundle model based on differences of the eCAPs simulated and the actual eCAPs measured.

10. The method of claim 1, further comprising performing validation of the ANF bundle model by:
  predicting perceptual psychophysical metrics of the living subject using the ANF bundle model;
  measuring model-estimated psychophysical metrics of the living subject; and
  calculating a correlation coefficient between the model-estimated psychophysical metrics and the perceptual psychophysical metrics.

11. The method of claim 10, wherein the psychophysical metrics includes channel overlap (CO) and tripolar thresholds.

12. A system for performing model-based cochlear implant programming (MOCIP) on a patient-customized electro-neural interface (ENI) model, comprising:
  a computing device having a processor and a storage device storing computer executable instructions, wherein the computer executable instructions, when being executed by the processor, causes the processor to perform operations comprising:
    localizing an electrode array of a cochlear implant (CI) implanted on a living subject and intracochlear structures of the living subject to determine patient-specific electrode positions of the CI and a patient-specific anatomy shape;
    generating a CI electric field model based on the patient-specific electrodes positions of the CI and the patient-specific anatomy shape; and
    establishing an auditory nerve fiber (ANF) bundle model using the CI electric field model, and estimating neural health of the living subject using the ANF bundle model, wherein the estimating the neural health of the living subject comprises:
      establishing the ANF bundle model with a plurality of ANF bundles, wherein each of the ANF bundles includes a plurality of fibers;
      simulating electrically evoked compound action potentials (eCAPs) in each of the fibers of the ANF bundles, wherein the eCAPs are measured by amplitude growth functions (AGFs), spread of excitation (SOE) functions, and refractory recovery functions (RRFs); and
      estimating, for the electrodes of the CI, the ANF bundles activated by each of the electrodes in response to a given stimulus; and
    performing validation of the ANF bundle model by:
      training the ANF bundle model using the eCAPs measured by one of the AGFs, SOE functions and RRFs; and
      estimating the neural health of the living subject using the trained ANF bundle model by simulating the eCAPs measured by a different one of the AGFs, SOE functions and RRFs.

13. The system of claim 12, wherein the patient-specific anatomy shape is determined by:
  obtaining a plurality of micro CT (μCT) images of a plurality of cochleae specimens;
  creating a non-rigid statistical shape model using the μCT images;
  fitting the non-rigid statistical shape model to an external boundary of the cochlea of the living subject in a computed tomography (CT) image of a cochlea of the living subject to localize positions of scala tympani (ST), scala vestibuli (SV) and modiolus of the living subject; and determining estimated positions of ANF bundles of the living subject.

14. The system of claim 13, wherein the estimated positions of the ANF bundles are determined by:
   delineating Rosenthal's Canal (RC) and internal auditory canal (IAC) in the µCT images;
   registering, with localized surfaces of the ST, the SV and the modiolus, estimations of fiber endpoints of the RC and the IAC delineated in the µCT images to the CT image using thin-plate splines; and
   tracing estimated fiber bundle paths of the ANF bundles from the fiber endpoints between the ST and the SV through the RC and out to the IAC.

15. The system of claim 13, wherein the patient-specific electrode positions of the CI are determined by identifying, from the µCT images, center lines of bright tubes or blobs representing the electrode array.

16. The system of claim 12, wherein the CI electric field model is generated by:
   generating a tissue resistivity map for the living subject based on the patient-specific electrodes positions of the CI and the patient-specific anatomy shape;
   inputting the tissue resistivity map to a finite difference model to simulate electric fields created in tissues of the living subject when electrodes of the CI are activated;
   performing electric field imaging (EFI) to measure the actual electric fields sensed by other electrodes of the electrodes of the CI when one of the electrodes of the CI is activated as a current source; and
   optimizing resistivity values of the tissues in the tissue resistivity map based on the electric field simulated by the finite difference model and the actual electric fields measured by EFI.

17. The system of claim 16, wherein the resistivity values of the tissues comprises are optimized by:
   comparing, for each of the electrodes of the CI, the electric fields simulated by the finite difference model and the actual electric fields measured by EFI; and
   in response to determining, for a specific electrode of the electrodes, the electric field simulated by the finite difference model corresponding to the specific electrode is significantly lower than the actual electric fields measured by EFI corresponding to the specific electrode, determining tissue growth occurs at the specific electrode, and adding a soft tissue layer around the specific electrode in the finite difference model.

18. The system of claim 12,
   wherein each of the ANF bundles includes a plurality of warmed Hodgkin-Huxley (wHH) fiber.

19. The system of claim 18, wherein the neural health of the living subject is further estimated by:
   measuring actual eCAPs for the electrodes of the CI; and
   tuning neural health parameters of the ANF bundle model based on differences of the eCAPs simulated and the actual eCAPs measured.

20. The system of claim 12, wherein the computer executable instructions, when being executed by the processor, further causes the processor to perform validation of the ANF bundle model by:
   predicting perceptual psychophysical metrics of the living subject using the ANF bundle model;
   measuring model-estimated psychophysical metrics of the living subject; and
   calculating a correlation coefficient between the model-estimated psychophysical metrics and the perceptual psychophysical metrics;
   wherein the psychophysical metrics includes at least one of channel overlap (CO) and tripolar thresholds.

21. A non-transitory tangible computer-readable medium storing computer executable instructions which, when executed by one or more processors, cause a method for performing model-based cochlear implant programming (MOCIP) on a living subject with a cochlear implant (CI) to determine stimulation settings of a patient-customized electro-neural interface (ENI) model to be performed, the method comprising:
   localizing an electrode array of the CI and intracochlear structures of the living subject to determine patient-specific electrode positions of the CI and a patient-specific anatomy shape;
   generating a CI electric field model based on the patient-specific electrodes positions of the CI and the patient-specific anatomy shape; and
   establishing an auditory nerve fiber (ANF) bundle model using the CI electric field model, and estimating neural health of the living subject using the ANF bundle model, wherein the estimating the neural health of the living subject comprises:
      establishing the ANF bundle model with a plurality of ANF bundles, wherein each of the ANF bundles includes a plurality of fibers;
      simulating electrically evoked compound action potentials (eCAPs) in each of the fibers of the ANF bundles, wherein the eCAPs are measured by amplitude growth functions (AGFs), spread of excitation (SOE) functions, and refractory recovery functions (RRFs); and
      estimating, for the electrodes of the CI, the ANF bundles activated by each of the electrodes in response to a given stimulus; and
   performing validation of the ANF bundle model by:
      training the ANF bundle model using the eCAPs measured by one of the AGFs, SOE functions and RRFs; and
      estimating the neural health of the living subject using the trained ANF bundle model by simulating the eCAPs measured by a different one of the AGFs, SOE functions and RRFs.

22. The non-transitory tangible computer-readable medium of claim 21, wherein the patient-specific anatomy shape is determined by:
   obtaining a plurality of micro CT (µCT) images of a plurality of cochleae specimens;
   creating a non-rigid statistical shape model using the µCT images;
   fitting the non-rigid statistical shape model to an external boundary of the cochlea of the living subject in a computed tomography (CT) image of a cochlea of the living subject to localize positions of scala tympani (ST), scala vestibuli (SV) and modiolus of the living subject; and
   determining estimated positions of ANF bundles of the living subject.

23. The non-transitory tangible computer-readable medium of claim 22, wherein the estimated positions of the ANF bundles are determined by:
   delineating Rosenthal's Canal (RC) and internal auditory canal (IAC) in the µCT images;
   registering, with localized surfaces of the ST, the SV and the modiolus, estimations of fiber endpoints of the RC and the IAC delineated in the μCT images to the CT image using thin-plate splines; and tracing estimated fiber bundle paths of the ANF bundles from the fiber endpoints between the ST and the SV through the RC and out to the IAC.

24. The non-transitory tangible computer-readable medium of claim 22, wherein the patient-specific electrode positions of the CI are determined by identifying, from the μCT images, center lines of bright tubes or blobs representing the electrode array.

25. The non-transitory tangible computer-readable medium of claim 21, wherein the CI electric field model is generated by:

generating a tissue resistivity map for the living subject based on the patient-specific electrodes positions of the CI and the patient-specific anatomy shape;

inputting the tissue resistivity map to a finite difference model to simulate electric fields created in tissues of the living subject when electrodes of the CI are activated;

performing electric field imaging (EFI) to measure the actual electric fields sensed by other electrodes of the electrodes of the CI when one of the electrodes of the CI is activated as a current source; and optimizing resistivity values of the tissues in the tissue resistivity map based on the electric field simulated by the finite difference model and the actual electric fields measured by EFI.

26. The non-transitory tangible computer-readable medium of claim 25, wherein the resistivity values of the tissues comprises are optimized by:

comparing, for each of the electrodes of the CI, the electric fields simulated by the finite difference model and the actual electric fields measured by EFI; and in response to determining, for a specific electrode of the electrodes, the electric field simulated by the finite difference model corresponding to the specific electrode is significantly lower than the actual electric fields measured by EFI corresponding to the specific electrode, determining tissue growth occurs at the specific electrode, and adding a soft tissue layer around the specific electrode in the finite difference model.

27. The non-transitory tangible computer-readable medium of claim 21, wherein each of the ANF bundles includes a plurality of warmed Hodgkin-Huxley (wHH) fiber.

28. The non-transitory tangible computer-readable medium of claim 27, wherein the neural health of the living subject is further estimated by:

measuring actual eCAPs for the electrodes of the CI; and tuning neural health parameters of the ANF bundle model based on differences of the eCAPs simulated and the actual eCAPs measured.

29. The non-transitory tangible computer-readable medium of claim 21, wherein the computer executable instructions, when being executed by the processor, further causes the processor to perform validation of the ANF bundle model by:

predicting perceptual psychophysical metrics of the living subject using the ANF bundle model;

measuring model-estimated psychophysical metrics of the living subject; and calculating a correlation coefficient between the model-estimated psychophysical metrics and the perceptual psychophysical metrics;

wherein the psychophysical metrics includes at least one of channel overlap (CO) and tripolar thresholds.

* * * * *